United States Patent
Bannasch et al.

(10) Patent No.: US 11,761,042 B2
(45) Date of Patent: Sep. 19, 2023

(54) METHODS OF DIAGNOSING INTERVERTEBRAL DISC DISEASE AND CHONDRODYSTROPHY IN CANINES

(71) Applicant: The Regents of the University of California, Oakland, CA (US)

(72) Inventors: Danika Bannasch, Davis, CA (US); Emily Brown, Davis, CA (US); Peter J. Dickinson, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 553 days.

(21) Appl. No.: 16/615,659

(22) PCT Filed: May 23, 2018

(86) PCT No.: PCT/US2018/034135
§ 371 (c)(1),
(2) Date: Nov. 21, 2019

(87) PCT Pub. No.: WO2018/222461
PCT Pub. Date: Dec. 6, 2018

(65) Prior Publication Data
US 2020/0208218 A1      Jul. 2, 2020

Related U.S. Application Data

(60) Provisional application No. 62/512,689, filed on May 30, 2017.

(51) Int. Cl.
| | |
|---|---|
| *C12Q 1/68* | (2018.01) |
| *C12P 19/34* | (2006.01) |
| *C12Q 1/6883* | (2018.01) |
| *C07K 14/50* | (2006.01) |

(52) U.S. Cl.
CPC ............ *C12Q 1/6883* (2013.01); *C07K 14/50* (2013.01); *C12Q 2600/156* (2013.01)

(58) Field of Classification Search
CPC ... C12Q 1/68; C12Q 1/6883; C12Q 2600/156
See application file for complete search history.

(56) References Cited

U.S. PATENT DOCUMENTS

2011/0097333 A1    4/2011  Clark et al.

FOREIGN PATENT DOCUMENTS

WO    2017019918    2/2017

OTHER PUBLICATIONS

Wang, X. et al "Analysis of randomly amplified polymorphic DNA (RAPD) for identifying genetic markers associated with canine hip dysplasia" Journal of Heredity, vol. 90, Issue 1, Jan. 1999, pp. 99-103 (Year: 1999).*
Heidi G. Parker, et al. "An Expressed Fgf4 Retrogene Is Associated with Breed-Defining Chondrodysplasia in Domestic Dogs" Science, vol. 325, Aug. 21, 2009, pp. 995-998 and Supplemental Material. (Year: 2009).*
Sandra R. Richardson, et al., "Diversity through duplication: Whole-genome sequencing reveals novel gene retrocopies in the human population" Bioessays 36: 475-481 (Year: 2014).*
John R. ten Bosch, et al., "Next-Generation Sequencing in Molecular Diagnostics" Molecular Diagnostics—Techniques and Applications for the Clinical Laboratory, 2010, pp. 59-67 (Year: 2010).*
Boer et al. (2009) "Regulation of the Nanog Gene by Both Positive and Negative cis-Regulatory Elements in Embryonal Carcinoma Cells and Embryonic Stem Cells" Molecular Reproduction and Development, 76(2):173-182.
Brown et al. (2017) "FGF4 retrogene on CFA12 is responsible for chondrodystrophy and intervertebral disc disease in dogs" PNAS, 114(43):11476-11481.
Frischknecht et al. (2013) "A COL 11A2 Mutation in Labrador Retrievers with Mild Disproportionate Dwarfism" PLoS One, 8(3):e60149, 9pgs.
Lark et al. (2006) "Genetic architecture of the dog: sexual size dimorphism and functional morphology" Trends in Genetics, 22(10):537-544.
Mogensen et al. (2011) "Genome-wide association study in Dachshund: identification of a major locus affecting intervertebral disc calcification" Journal of Heredity, 102(S1):S81-S86.
Parker et al. (2009) "An expressed fgf4 retrogene is associated with breed-defining chondrodysplasia in domestic dogs" Science, 325(5943):995-998.
Quignon et al. (2009) "Fine Mapping a Locus Controlling Leg Morphology in the Domestic Dog" Cold Spring Harbor Symposia on Quantitative Biology, 76:327-333.
Smolders et al. (2012) "Intervertebral disc degeneration in the dog. Part 2: chondrodystrophic and non-chondrodystrophic breeds" Vet J., 8pgs.

* cited by examiner

*Primary Examiner* — Stephen T Kapushoc
(74) *Attorney, Agent, or Firm* — Brian E. Davy; Bozicevic, Field & Francis LLP

(57) ABSTRACT

Provided are compositions and methods for identifying a canine suffering from or at risk of suffering from skeletal dysplasia (SD) and/or intervertebral disc disease (IVDD) by detecting a retrogene insertion encoding canine fibroblast growth factor 4 (FGF4) on canine chromosome 12.

12 Claims, 11 Drawing Sheets
Specification includes a Sequence Listing.

Fig. 1A-B

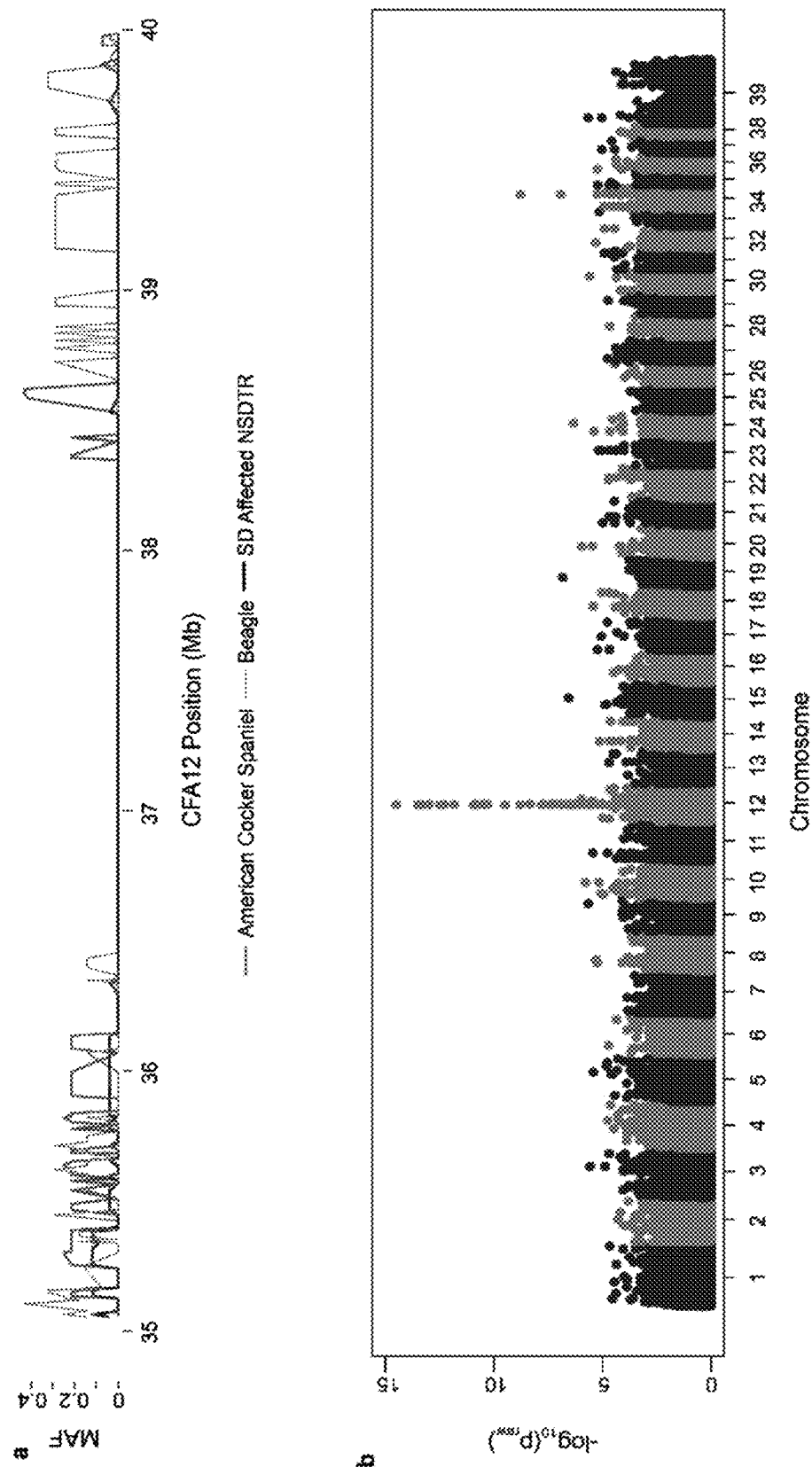
Fig. 3A-B

Fig. 6A-C

METHODS OF DIAGNOSING INTERVERTEBRAL DISC DISEASE AND CHONDRODYSTROPHY IN CANINES

CROSS-REFERENCE TO RELATED APPLICATIONS

This application claims the benefit of U.S. Provisional Application No. 62/512,689, filed on May 30, 2017, which is hereby incorporated herein by reference in its entirety.

INCORPORATION BY REFERENCE OF SEQUENCE LISTING

A Sequence Listing is provided herewith as a text file, "UCDVP147WO_SL.txt" created on Aug. 17, 2018, and having a size of 17 KB. The contents of the text file are incorporated by reference herein in their entirety.

STATEMENT OF GOVERNMENTAL SUPPORT

This invention was made with government support under Grant No. NIH 5 T32 OD010931 2016_20F, awarded by the National Institutes of Health. The government has certain rights in the invention.

BACKGROUND

Variation in domestic dog (Canis familiaris, CFA) morphology has long fascinated both scientists and pet owners. Domestication of the dog from the wolf and the subsequent variation in size and shape within purebred dog breeds is a remarkable feat of animal breeding and selection. One of the most extreme examples of dog breed differences is in limb length, as extremely short limbs define many breeds. This morphological feature is present in breeds from all over the world and from all American Kennel Club groups, indicating that the underlying genetic causes are likely very old.

Extensive examination of growth plates has been performed on many of these short-legged dog breeds (Dachshund, Pekingese, French Bulldog, Spaniels, Beagle), as these breeds are also prone to intervertebral disc disease (IVDD) (1-3). Histopathological analysis of the bones of puppies from these breeds demonstrated that their short stature is due to defects in endochondral ossification, the process whereby cartilage is replaced with bone in the developing limb. The long bone growth plates show disorganization of the proliferative zone and reduction in the depth of the maturation zone (1-4). In addition to the long bones, similar but more subtle changes exist in endochondral ossification of the vertebral bodies (1,2).

The intervertebral disc (IVD) is composed of an outer fibrous basket, called the annulus fibrosis, made of 70% collagen and an inner gel-like layer that is a remnant of the embryonic notochord, called the nucleus pulposus (5). Together, these structures and the cartilaginous endplates allow for flexibility of the vertebral column. In chondrodystrophic dogs, the nucleus pulposus is gradually replaced by chondrocyte-like cells in chondroid metaplasia (or metamorphosis) that occurs between birth and 1 year of age (1,2). Recent studies have shown that in advanced stages of degeneration in nonchondrodystrophoid dogs there is also replacement of notochordal cells by chondrocyte-like cells, similar to the changes observed in chondrodystrophoid dogs, although this happens at an older age (3, 6-10). The replacement of the nucleus pulposus with chondrocyte like cells is seen in humans, and chondrodystrophoid breeds have been proposed as models for human degenerative disc disease (3, 7, 11, 12).

Hansen described the two different types of canine IVD prolapse as type I and type II. Type I occurs exclusively in chondrodystrophic breeds and is characterized by premature degeneration of all discs in young dogs. In contrast, Type II occurs in older dogs and is usually limited to a single disc with only partial protrusion. In Type I disc disease the calcified nucleus pulposus may undergo an explosive herniation through the annulus fibrous into the vertebral canal, resulting in inflammation and hemorrhage and causing severe pain and neurological dysfunction (1, 2). In veterinary hospital population studies, breeds with a significant increased risk of IVDD include the Beagle, Cocker Spaniel, Dachshund, French Bulldog, Lhasa Apso, Pekingese, Pembroke Welsh Corgi, and Shih Tzu (13-15). Pet insurance data suggests a conservative "lifetime prevalence" for IVDD in dogs of 3.5% in the overall population; however, in the chondrodystrophic breed with the highest risk, the Dachshund, the "lifetime prevalence" is between 20-62% with a mortality rate of 24% (9, 16-19). The effect of this disease on dogs and the financial burden to pet owners is enormous.

Skeletal dysplasia (SD), a general term to classify abnormalities of growth and development of cartilage and/or bone resulting in various forms of short stature, occurs in humans and dogs in many forms (20). With advances in molecular genetics, many of the diseases in humans are being reclassified based on the specific underlying causative mutations (21). To a lesser degree, progress has also been made in understanding the molecular nature of SD and the extreme interbreed limb length variation observed in dogs (22-25). While the mutations causing some subtypes of SD in dogs have been determined, there are still many unexplained types of SD observed within and across dog breeds.

In 2009 the genetic basis for extreme differences in limb length in dogs was investigated by Parker et al. using an across breed genome-wide association approach (26). They determined that a FGF4 retrogene insertion on CFA18 was responsible for the "chondrodysplasia" phenotype in a number of breeds, such as the Basset Hound, Pembroke Welsh Corgi, and Dachshund. However, the FGF4 retrogene insertion on CFA18 failed to explain breeds such as the American Cocker Spaniel, Beagle, and French Bulldog, that in addition to Dachshunds, were the breeds originally classified as chondrodystrophoid based on histopathologic and morphologic analysis by Hansen and Braund (1, 3). The FGF gene family has similarly been implicated in SD in humans, with mutations in FGFR3 found to be responsible for achondrodysplasia, the most common form of dwarfism, characterized by shortened limbs and abnormal vertebrae and IVDs (21, 27-31). FGF genes are involved in a number of embryological development processes, and specific levels of ligand and receptor are key for appropriate growth and development (32-34).

SUMMARY

In one aspect, provided are reaction mixtures. In some embodiments, the reaction mixtures comprise (i) a biological sample from a canine comprising a nucleic acid template, and (ii) one or more oligonucleotide pairs configured to detect the presence or absence of a retrogene insertion encoding canine fibroblast growth factor 4 (FGF4) on canine chromosome 12. In some embodiments, the retrogene comprises about 3.2 kilobases (kb). In some embodiments, retrogene insertion is inserted at a target site duplication sequence located at chr12:33,710,168-33,710,178 (canFam3). In some embodiments, the oligonucleotide pairs detect the 5'-end and/or the 3'-end of the retrogene insertion. In some embodiments, the 5'-end of the retrogene insertion encoding canine fibroblast growth factor 4 (FGF4) comprises a nucleic acid sequence having at least 90% sequence identity, e.g., at least 91%, 92%, 93%, 94%, 95%, 96%, 97%, 98%, 99%, or 100% sequence identity, to nucleic acid residues 1002-2001 SEQ ID NO:1. In some embodiments, the one or more oligonucleotide pairs are configured or designed or constructed to detect the 3'-end of the retrogene insertion located at nucleic acid residue 1002 of SEQ ID NO:1. In some embodiments, an oligonucleotide in the one or more oligonucleotide pairs hybridizes to a sequence segment within nucleic acid residues 1-1001 of SEQ ID NO:2. In some embodiments, the 3'-end of the retrogene insertion encoding canine fibroblast growth factor 4 (FGF4) comprises a nucleic acid sequence having at least 90% sequence identity, e.g., at least 91%, 92%, 93%, 94%, 95%, 96%, 97%, 98%, 99%, or 100% sequence identity, to nucleic acid residues 1-1000 SEQ ID NO:2. In some embodiments, the one or more oligonucleotide pairs are configured to detect the 3'-end of the retrogene insertion located at nucleic acid residue 1000 of SEQ ID NO:2. In some embodiments, an oligonucleotide in the one or more oligonucleotide pairs hybridizes to a sequence segment within nucleic acid residues 1001-2000 of SEQ ID NO:2. In some embodiments, the one or more oligonucleotide pairs comprise one or more forward primers selected from the group consisting of: ACAGCTGGCATGGTCAGTTA (SEQ ID NO: 13), GTGTTTGCATGGAGGAAGGT (SEQ ID NO:3), CTGAGCAAGAACGGGAAGAC (SEQ ID NO:4), AGCCTGATGGCTGGACTGTA (SEQ ID NO:5) and GTCCGTGCGGTGAAATAAAA (SEQ ID NO:6) and one or more reverse primers selected from the group consisting of TGCTGTAGATTTTGAGGTGTCTT (SEQ ID NO:7), CCTGATTTTGAGACAGCCAAA (SEQ ID NO:8), TTGATGCCCAGGAGGTAGTC (SEQ ID NO:9) and TGAGTGGGTTAAGGGTTTCG (SEQ ID NO:10). In some embodiments, the one or more oligonucleotides comprise one or more forward primers selected from the group consisting of:

```
                                     (SEQ ID NO: 13)
ACAGCTGGCATGGTCAGTTA
and (SEQ ID NO: 6)
GTCCGTGCGGTGAAATAAAA
and reverse primer
                                      (SEQ ID NO: 7)
TGCTGTAGATTTTGAGGTGTCTT.
```

In some embodiments, the nucleic acid template comprises genomic DNA. In some embodiments, the reaction mixture further comprises a polymerase and dNTPs.

In another aspect, provided are kits. In some embodiments, the kits comprise one or more oligonucleotide pairs that specifically identify the presence or absence of a retrogene insertion encoding canine fibroblast growth factor 4 (FGF4) on canine chromosome 12. In some embodiments, the oligonucleotide pairs detect the 5'-end and/or the 3'-end of the retrogene insertion. In some embodiments, the 5'-end of the retrogene insertion encoding canine fibroblast growth factor 4 (FGF4) comprises a nucleic acid sequence having at least 90% sequence identity, e.g., at least 91%, 92%, 93%, 94%, 95%, 96%, 97%, 98%, 99%, or 100% sequence identity, to nucleic acid residues 1002-2001 SEQ ID NO:1. In some embodiments, the one or more oligonucleotide pairs are configured to detect the 5'-end of the retrogene insertion located at nucleic acid residue 1002 of SEQ ID NO:1. In some embodiments, an oligonucleotide in the one or more oligonucleotide pairs hybridizes to a sequence segment within nucleic acid residues 1-1001 of SEQ ID NO:1. In some embodiments, the 3'-end of the retrogene insertion encoding canine fibroblast growth factor 4 (FGF4) comprises a nucleic acid sequence having at least 90% sequence identity, e.g., at least 91%, 92%, 93%, 94%, 95%, 96%, 97%, 98%, 99%, or 100% sequence identity, to nucleic acid residues 1-1000 SEQ ID NO:2. In some embodiments, the one or more oligonucleotide pairs are configured to detect the 3'-end of the retrogene insertion located at nucleic acid residue 1000 of SEQ ID NO:2. In some embodiments, an oligonucleotide in the one or more oligonucleotide pairs hybridizes to a sequence segment within nucleic acid residues 1001-2000 of SEQ ID NO:2. In some embodiments, the one or more oligonucleotide pairs comprise one or more forward primers selected from the group consisting of: ACAGCTGGCATGGTCAGTTA (SEQ ID NO: 13), GTGTTTGCATGGAGGAAGGT (SEQ ID NO:3), CTGAGCAAGAACGGGAAGAC (SEQ ID NO:4), AGCCTGATGGCTGGACTGTA (SEQ ID NO:5) and GTCCGTGCGGTGAAATAAAA (SEQ ID NO:6) and one or more reverse primers selected from the group consisting of TGCTGTAGATTTTGAGGTGTCTT (SEQ ID NO:7), CCTGATTTTGAGACAGCCAAA (SEQ ID NO:8), TTGATGCCCAGGAGGTAGTC (SEQ ID NO:9) and TGAGTGGGTTAAGGGTTTCG (SEQ ID NO:10).

In another aspect, provided are solid supports. In some embodiments, the solid supports are attached to one or more oligonucleotides that specifically identify the presence or absence of a retrogene insertion encoding canine fibroblast growth factor 4 (FGF4) on canine chromosome 12. In some embodiments, the solid support is attached to an oligonucleotide that hybridizes to the 5'-end of the retrogene insertion located at nucleic acid residue 1002 of SEQ ID NO:1. In some embodiments, the solid support is attached to an oligonucleotide that hybridizes to the 3'-end of the retrogene insertion located at nucleic acid residue 1000 of SEQ ID NO:2. In some embodiments, the solid support is attached to an oligonucleotide having at least about 80% sequence identity, e.g., at least 81%, 82%, 83%, 84%, 85%, 86%, 87%, 88%, 89%, 90%, 91%, 92%, 93%, 94%, 95%, 96%, 97%, 98%, 99%, or 100% sequence identity, to SEQ ID NO:11 and/or SEQ ID NO:12. In some embodiments, the solid support is a microarray. In some embodiments, the solid support is a mounted tissue sample. Further provided are kits comprising the solid support as described above and herein.

In a further aspect, provided are methods for identifying a canine suffering from or at risk of suffering from skeletal dysplasia (SD) and/or intervertebral disc disease (IVDD). In some embodiment, the methods comprise: a) obtaining a biological sample comprising a nucleic acid template from the canine; b) determining the presence or absence of a retrogene insertion encoding canine fibroblast growth factor 4 (FGF4) on canine chromosome 12; and c) selecting a canine comprising the retrogene insertion identifies a canine suffering from or at risk of suffering from skeletal dysplasia (SD) and/or intervertebral disc disease (IVDD) relative to canine that does not have the retrogene insertion encoding canine fibroblast growth factor 4 (FGF4) on canine chromosome 12. In a related aspect, provided are methods for identifying a canine with reduced risk of suffering from skeletal dysplasia (SD) and/or intervertebral disc disease (IVDD). In some embodiments, the methods comprise: a) obtaining a biological sample comprising a nucleic acid template from the canine; b) determining the presence or absence of a retrogene insertion encoding canine fibroblast growth factor 4 (FGF4) on canine chromosome 12; and c) selecting a canine that does not comprise the retrogene insertion identifies a canine with reduced risk of suffering from skeletal dysplasia (SD) and/or intervertebral disc disease (IVDD) relative to canine that has the retrogene insertion encoding canine fibroblast growth factor 4 (FGF4) on canine chromosome 12. In some embodiments, the retrogene comprises about 3.2 kilobases (kb). In some embodiments, the retrogene insertion is inserted at a target site duplication sequence located at chr12:33,710,168-33,710,178 (canFam3). In some embodiments, the determining step employs one or more polynucleotides configured to detect the 5'-end and/or the 3'-end of the retrogene insertion. In some embodiments, the 5'-end of the retrogene insertion encoding canine fibroblast growth factor 4 (FGF4) comprises a nucleic acid sequence having at least 90% sequence identity, e.g., at least 91%, 92%, 93%, 94%, 95%, 96%, 97%, 98%, 99%, or 100% sequence identity, to nucleic acid residues 1002-2001 SEQ ID NO:1. In some embodiments, the one or more polynucleotides are configured to detect the 5'-end of the retrogene insertion located at nucleic acid residue 1002 of SEQ ID NO:1. In some embodiments, one polynucleotide hybridizes to a sequence segment within nucleic acid residues 1-1001 of SEQ ID NO:1. In some embodiments, the 3'-end of the retrogene insertion encoding canine fibroblast growth factor 4 (FGF4) comprises a nucleic acid sequence having at least 90% sequence identity, e.g., at least 91%, 92%, 93%, 94%, 95%, 96%, 97%, 98%, 99%, or 100% sequence identity, to nucleic acid residues 1-1000 SEQ ID NO:2. In some embodiments, the one or more polynucleotides are configured to detect the 3'-end of the retrogene insertion located at nucleic acid residue 1000 of SEQ ID NO:2. In some embodiments, one polynucleotide hybridizes to a sequence segment within nucleic acid residues 1001-2000 of SEQ ID NO:2. In some embodiments, the SD/IVDD genotype is detected by an amplification reaction using polynucleotides that identify the presence or absence of the CFA 12 FGF4 retrogene insertion. In some embodiments, the amplification reaction is selected from the group consisting of polymerase chain reaction (PCR), strand displacement amplification (SDA), nucleic acid sequence based amplification (NASBA), rolling circle amplification (RCA), T7 polymerase mediated amplification, T3 polymerase mediated amplification and SP6 polymerase mediated amplification. In some embodiments, a portion of the retrogene insertion sequence is specifically amplified using one or more forward primers selected from the group consisting of: ACAGCTGGCATGGTCAGTTA (SEQ ID NO:13), GTGTTTGCATGGAGGAAGGT (SEQ ID NO:3), CTGAGCAAGAACGGGAAGAC (SEQ ID NO:4), AGCCTGATGGCTGGACTGTA (SEQ ID NO:5) and GTCCGTGCGGTGAAATAAAA (SEQ ID NO:6) and one or more reverse primers selected from the group consisting of TGCTGTAGATTTTGAGGTGTCTT (SEQ ID NO:7), CCTGATTTTGAGACAGCCAAA (SEQ ID NO:8), TTGATGCCCAGGAGGTAGTC (SEQ ID NO:9) and TGAGTGGGTTAAGGGTTTCG (SEQ ID NO:10). In some embodiments, a portion of the retrogene insertion sequence is specifically amplified using one or more forward primers selected from the group consisting of: ACAGCTGGCATGGTCAGTTA (SEQ ID NO:13) and GTCCGTGCGGTGAAATAAAA (SEQ ID NO:6) and reverse primer TGCTGTAGATTTTGAGGTGTCTT (SEQ ID NO:7). In some embodiments, the SD/IVDD genotype is detected by hybridization using polynucleotides which identify the presence or absence of the CFA 12 FGF4 retrogene insertion. In some embodiments, the SD/IVDD genotype is detected by sequencing. In some embodiments, the canine is a domesticated canine. In some embodiments, the canine is of a breed having a predisposition to chondrodystrophy. In some embodiments, the canine is a purebred or mix from a breed selected from the group consisting of American Cocker Spaniel, Basset Hound, Beagle, Cardigan Welsh Corgi, Chesapeake Bay Retriever, Chihuahua, Coton de Tulear, Dachshund, English Springer Spaniel, French Bulldog, Jack Russell Terrier, Miniature Schnauzer, Nova Scotia Duck Tolling Retriever, Pekingese, Pembroke Welsh Corgi, Poodle, Portuguese Water Dog, Scottish Terrier, Shih Tzu, and mixtures thereof. In varying, the canine is a purebred or mix from a breed selected from the group consisting of American Cocker Spaniel, Basset Hound, Beagle, Corgi, Dachshund, French bulldog, Nova Scotia Duck Tolling Retriever, and Pekingese.

Definitions

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry and nucleic acid chemistry and hybridization described below are those well-known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Green and Sambrook et al. MOLECULAR CLONING: A LABORATORY MANUAL, 4th ed. (2012) Cold Spring Harbor Laboratory Press, Cold Spring Harbor, N.Y. and Ausubel, ed., Current Protocols in Molecular Biology, 1990-2017, John Wiley Interscience), which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

"Chondrodystrophy" refers to defects in long bone and vertebral body endochondral ossification and abnormal intervertebral discs that prematurely degenerate and calcify, which ultimately can lead to disc herniation and paralysis referred to as Hansen's Type I intervertebral disc disease (IVDD). Reviewed in, e.g., Smith, et al., *Vet Comp Orthop Traumatol.* (2016) 29(3):220-6; Smolders, et al., *Vet J.* (2013) 195(3):292-9; Bergknut, et al., *Vet J.* (2013) 195(3): 282-91; Bergknut, et al., *Vet J.* (2013) 195(2):156-63 and Beachley, et al., *J Am Vet Med Assoc.* (1973) 163(3):283-4.

"Chondrodysplasia" refers to disproportionate dwarfism.

As used herein, the terms "dog," "canine" and "Canis lupus familiaris" are used interchangeably.

The term "gene" means the segment of DNA involved in producing a polypeptide chain; it includes regions preceding and following the coding region (leader and trailer) as well as intervening sequences (introns) between individual coding segments (exons).

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A "variant" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variant" are used interchangeably herein to describe such variants. As used herein, the term "variant" in the singular is to be construed to include multiple variances; i.e., two or more nucleotide additions, deletions and/or substitutions in the same polynucleotide. A "point mutation" refers to a single substitution of one nucleotide for another.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point I for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "identical" or percent "identity," in the context of two or more nucleic acids or polypeptide sequences, refer to two or more sequences or subsequences that are the same or have a specified percentage of amino acid residues or nucleotides that are the same (i.e., share at least about 80% identity, for example, at least about 85%, 90%, 91%, 92%, 93%, 94%, 95%, 96%, 97%, 98%, 99% identity over a specified region to a reference sequence, e.g., SEQ ID NOs:1-11 and the other nucleic acid sequences provided herein), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, for example, over a region that is 50-100 amino acids or nucleotides in length, or over the full-length of a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to canine FGF4 nucleic acids and proteins, the BLAST and BLAST 2.0 algorithms and the default parameters discussed below are used.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Array" as used herein refers to a solid support comprising attached nucleic acid or peptide probes. Arrays typically comprise a plurality of different nucleic acid or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., Science, 251:767-777 (1991). These arrays may generally be produced using mechanical synthesis methods or light directed synthesis methods which incorporate a combination of photolithographic methods and solid phase synthesis methods. Techniques for the synthesis of these arrays using mechanical synthesis methods are described in, e.g., U.S. Pat. No. 5,384,261. Arrays may comprise a planar surface or may be nucleic acids or peptides on beads, gels, polymeric surfaces, fibers such as fiber optics, glass or any other appropriate substrate as described in, e.g., U.S. Pat. Nos. 5,770,358, 5,789,162, 5,708,153, 6,040,193 and 5,800, 992. Arrays may be packaged in such a manner as to allow for diagnostics or other manipulation of an all-inclusive device, as described in, e.g., U.S. Pat. Nos. 5,856,174 and 5,922,591.

BRIEF DESCRIPTION OF THE DRAWINGS

FIGS. 1A-C illustrate Skeletal Dysplasia (SD) in the Nova Scotia Duck Tolling Retriever (NSDTR): a) Picture and lateral thoracic limb radiograph of unaffected NSDTRs (ages 1 year old and 4 years old, respectively). b) Left panels depict picture and lateral thoracic limb radiograph of mildly SD affected NSDTRs (ages 4 years old and 2 years old, respectively); right panels depict picture and lateral thoracic limb radiograph of more severely SD affected NSDTRs (ages 3 years old and 6 months old, respectively). Relative to the unaffected dog, the mildly SD affected NSDTR has cranial bowing of the radius. Radiographic changes in the more severely SD NSDTR include moderate cranial bowing of the radius, physeal widening, and incongruity of the elbow joint with the shape of the semi-lunar notch of the ulna being elongated. Pictures and radiographs are representatives of each phenotype and not paired (i.e. the radiographs are not of the dogs pictured). c) SD in NSDTR GWAS: Manhattan plot showing log 10 of the raw p-values for each genotyped SNP by chromosome (x-axis). After SNP quality control, there were 106,303 SNPs for Chi square analysis. Genomic inflation was 1.01604. Line denotes genome-wide significance based on Bonferroni corrected p-values.

FIGS. 3A-C illustrate across breed investigation of SD-IVDD locus: a) Minor allele frequency on the y-axis and base pair on CFA12 on the x-axis plotted by breed: SD affected NSDTR (n=13), American Cocker Spaniel (n=7), and Beagle (n=14). b) Manhattan plot for the SNPs in the across breed IVDD GWAS showing −log 10 of the raw p-values (y-axis) for each genotyped SNP by chromosome (x-axis). After SNP quality control, there were 126,020 SNPs for Chi square analysis. Genomic inflation was 1.6339. c) SNPs in 5 Mb region surrounding most highly associated SNP (chr12:36,909,311 (canFam2)) plotted by base pair on the x-axis and p-value on the y-axis. SNPs have been pruned from analysis using recommended criteria by Kierczak et al. (37). SNPs are color-coded by $r^2$ value to show the extent of linkage disequilibrium.

(y-axis). Only genotyped dogs with weights available (n=376) were included in the figure. Dogs are color-coded by genotype status.

Figure 8:
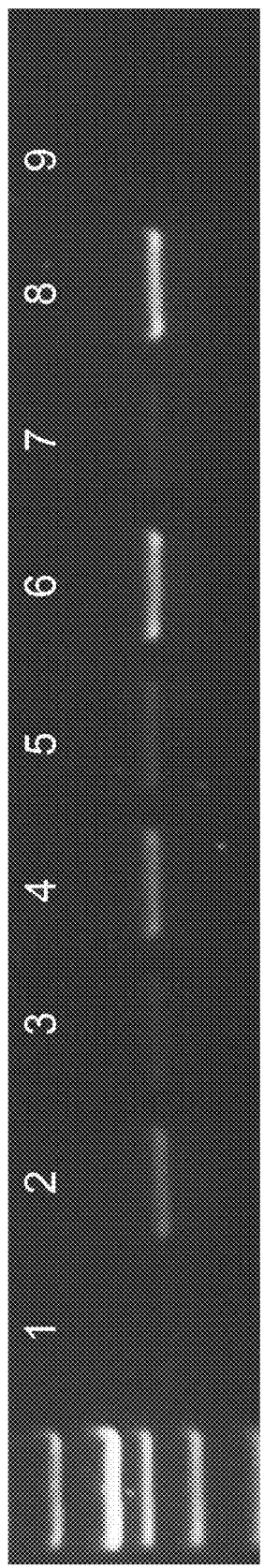

FIG. 8 illustrates semi-quantitative RT-PCR for FGF4 across tissues in a case and control. Lane order: Ladder; 1) Control VB (Cane Corso); 2) Case VB (Beagle); 3) Control IVD (Cane Corso); 4) Case IVD (Beagle); 5) Control skeletal muscle (Labrador retriever); 6) Case skeletal muscle (Beagle); 7) Control testis (Labrador retriever); 8) Case testis (Beagle); 9) Negative control.

Figure 9:
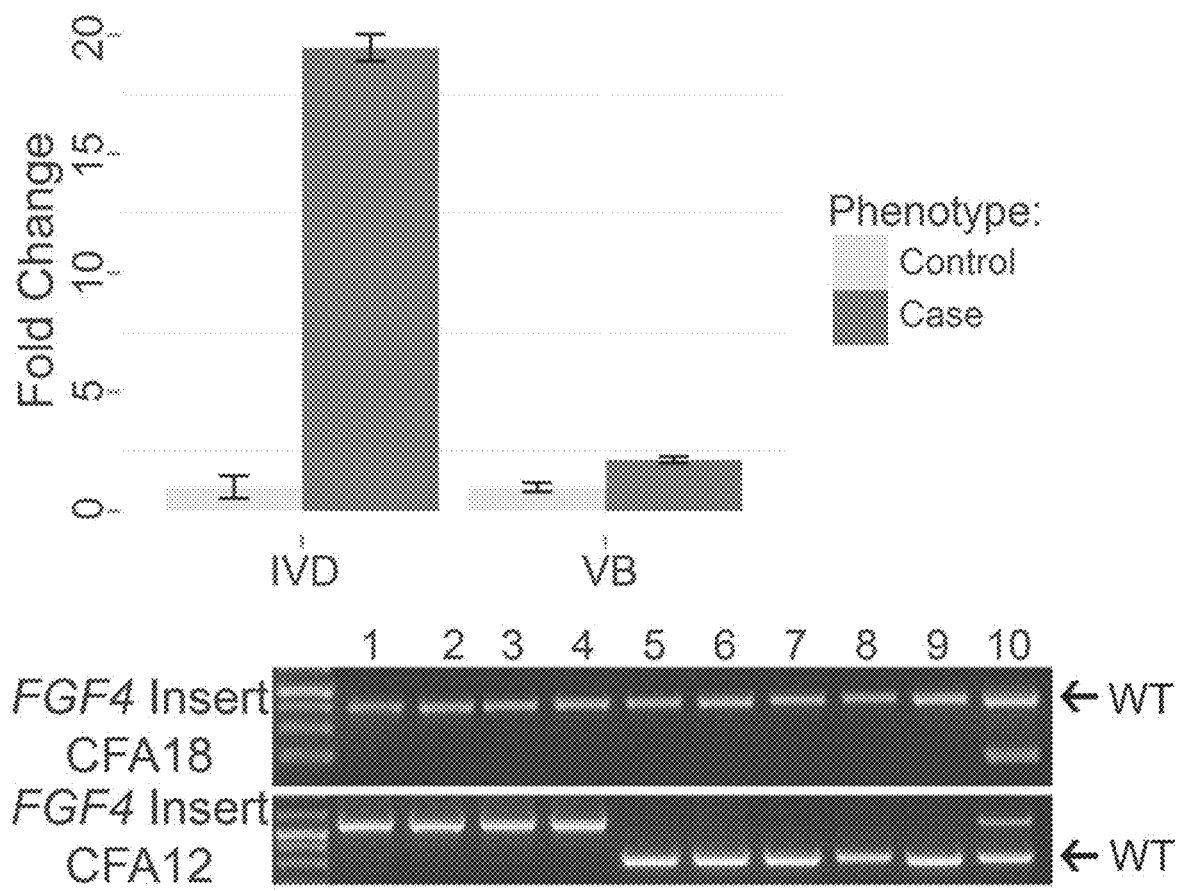

FIG. 9 illustrates FGF4 expression: Bar graph depicting fold change differences in FGF4 expression between controls and IVDD cases in neonatal IVD and VB. FGF4 expression was 19.47× higher (p=0.02857) in IVD and 2.16× higher (p=0.02857) in VB of cases compared to controls. Error bars representative of standard error of measurement for each group. Gels depict genotypes of 4 cases (Beagles) and 5 controls (1 Rottweiler and 4 Cane Corso) used in qRT-PCR analysis. The five controls were wild type, meaning they lacked the FGF4 insert at both the CFA12 and CFA18 locations; however, the cases, while wild type for the CFA18 FGF4 insert, were homozygous mutant at the CFA12 locus. Lanes: 1-4: Beagle cases; 5-9: Cane Corso controls; 10: heterozygous control; 11: negative control.

DETAILED DESCRIPTION

1. Introduction

Chondrodystrophy in dogs is defined by dysplastic, shortened long bones and premature degeneration and calcification of intervertebral discs. Independent genome-wide association analyses for skeletal dysplasia (short limbs) within a single breed (pBonferroni=0.0072) and intervertebral disc disease (IVDD) across breeds) (pBonferroni=$4.02 \times 10^{-10}$ both identified a significant association to the same region on CFA12. Whole genome sequencing identified a highly expressed FGF4 retrogene within this shared region. The FGF4 retrogene segregated with limb length and had an odds ratio of 51.23 (95% CI=46.69, 56.20) for IVDD. Long bone length in dogs is a unique example of multiple disease-causing retrocopies of the same parental gene in a mammalian species. FGF signaling abnormalities have been associated with skeletal dysplasia in humans, and our findings present opportunities for both selective elimination of a medically and financially devastating disease in dogs and further understanding of the ever-growing complexity of retrogene biology.

In this study, genome-wide association analysis in a cohort of Nova Scotia Duck Tolling Retrievers (NSDTRs) with and without severe SD identified a significant association on CFA12 due to a 12 Mb associated haplotype, of which 1.9 Mb was found to be shared in chondrodystrophoid breeds. Subsequent genome-wide association analysis of Hansen's type I IVDD across breeds localized the same 1.9 Mb region on CFA12, suggesting that the locus responsible for SD in the NSDTR is also responsible for type I IVDD and the chondrodystrophoid phenotype across dog breeds. A previous genetic investigation of IVDD in Dachshunds and limb length morphology in Portuguese Water Dogs both identified the same CFA12 locus; however, neither study reported a causative mutation (35,36). The present compositions and methods are based, in part, on the discovery of a second FGF4 retrogene insertion (chr12:33.7 Mb (canFam3)) in the canine genome and show that it is not only responsible for SD in the NSDTR, but also chondrodystrophy, including the predisposition to Hansen's type I IVDD, across all dog breeds.

2. Reaction Mixtures

Provided are reaction mixtures for identifying the presence or absence of a retrogene insertion encoding canine fibroblast growth factor 4 (FGF4) on canine chromosome 12, as correlated with canine skeletal dysplasia (SD) and/or intervertebral disc disease (IVDD). In some embodiments, the reaction mixtures comprise (i) a biological sample from an canine comprising a nucleic acid template, and (ii) one or more oligonucleotide pairs configured to detect the presence or absence of a retrogene insertion encoding canine fibroblast growth factor 4 (FGF4) on canine chromosome 12. In some embodiments, the retrogene comprises about 3.2 kilobases (kb). In some embodiments, retrogene insertion is inserted at a target site duplication sequence located at chr12:33,710,168-33,710,178 (canFam3). In some embodiments, the oligonucleotide pairs detect the 5'-end and/or the 3'-end of the retrogene insertion. In some embodiments, the 3'-end of the retrogene insertion encoding canine fibroblast growth factor 4 (FGF4) comprises a nucleic acid sequence having at least 90% sequence identity, e.g., at least 91%, 92%, 93%, 94%, 95%, 96%, 97%, 98%, 99%, or 100% sequence identity, to nucleic acid residues 1002-2001 SEQ ID NO:1. In some embodiments, the one or more oligonucleotide pairs are configured or designed or constructed to detect the 3'-end of the retrogene insertion located at nucleic acid residue 1002 of SEQ ID NO:1. In some embodiments, the 5'-end of the retrogene insertion encoding canine fibroblast growth factor 4 (FGF4) comprises a nucleic acid sequence having at least 90% sequence identity, e.g., at least 91%, 92%, 93%, 94%, 95%, 96%, 97%, 98%, 99%, or 100% sequence identity, to nucleic acid residues 1-1000 SEQ ID NO:2. In some embodiments, the one or more oligonucleotide pairs are configured to detect the 5'-end of the retrogene insertion located at nucleic acid residue 1000 of SEQ ID NO:2. In some embodiments, the one or more oligonucleotide pairs comprise one or more forward primers selected from the group consisting of: ACAGCTGGCATGGTCAGTTA (SEQ ID NO:13), GTGTTTGCATGGAGGAAGGT (SEQ ID NO:3), CTGAGCAAGAACGGGAAGAC (SEQ ID NO:4), AGCCTGATGGCTGGACTGTA (SEQ ID NO:5) and GTCCGTGCGGTGAAATAAAA (SEQ ID NO:6) and one or more reverse primers selected from the group consisting of TGCTGTAGATTTTGAGGTGTCTT (SEQ ID NO:7), CCTGATTTTGAGACAGCCAAA (SEQ ID NO:8), TTGATGCCCAGGAGGTAGTC (SEQ ID NO:9) and TGAGTGGGTTAAGGGTTTCG (SEQ ID NO:10). In some embodiments, the one or more oligonucleotides comprise one or more forward primers selected from the group consisting of: ACAGCTGGCATGGTCAGTTA (SEQ ID NO:13) and GTCCGTGCGGTGAAATAAAA (SEQ ID NO:6) and reverse primer TGCTGTAGATTTTGAGGTGTCTT (SEQ ID NO:7). In some embodiments, the nucleic acid template comprises genomic DNA.

The nucleic acid template in the biological sample can comprise genomic DNA. In some embodiments, the reaction mixtures further can comprise appropriate buffers, salts, polymerases, reverse-transcriptases, dNTPs, nuclease inhibitors, and other reagents to facilitate amplification and/or detection reactions (e.g., primers, labels) for amplifying the canine FGF4 retrogene from genomic DNA.

3. Solid Supports

Further provided are solid supports attached to one or more polynucleotides or oligonucleotides that specifically detect the presence or absence of a retrogene insertion encoding canine fibroblast growth factor 4 (FGF4) on canine chromosome 12, found to correlate with canine skeletal dysplasia (SD) and/or intervertebral disc disease (IVDD).

In some embodiments, the solid supports are attached to one or more oligonucleotides that specifically identify the presence or absence of a retrogene insertion encoding canine fibroblast growth factor 4 (FGF4) on canine chromosome 12. In some embodiments, the solid support is attached to an oligonucleotide that hybridizes to the 5'-end of the retrogene insertion located at nucleic acid residue 1002 of SEQ ID NO: 1. In some embodiments, the solid support is attached to an oligonucleotide that hybridizes to the 3'-end of the retrogene insertion located at nucleic acid residue 1000 of SEQ ID NO:2. In some embodiments, the solid support is attached to an oligonucleotide having at least about 80% sequence identity, e.g., at least 81%, 82%, 83%, 84%, 85%, 86%, 87%, 88%, 89%, 90%, 91%, 92%, 93%, 94%, 95%, 96%, 97%, 98%, 99%, or 100% sequence identity, to SEQ ID NO:11 and/or SEQ ID NO:12. In some embodiments, the solid support is a microarray. In some embodiments, the solid support is a mounted tissue sample.

In certain embodiments, the solid support is a microarray, e.g., a genotyping array. Microarrays suitable for genotyping are commercially available, e.g., Axiom™ Canine Genotyping Array from ThermoFisher (thermofisher.com); CanineHD Whole-Genome Genotyping BeadChip from Illumina (illumina.com). In some embodiments, the one or more polynucleotides or oligonucleotides that specifically identify the presence or absence of a retrogene insertion encoding canine fibroblast growth factor 4 (FGF4) on canine chromosome 12 can be further or additionally attached to a canine genotyping array, e.g., an Axiom™ Canine Genotyping Array from ThermoFisher (thermofisher.com) or a CanineHD Whole-Genome Genotyping BeadChip from Illumina. Construction and use of microarrays is known in the art and described, e.g., in Bowtell and Sambrook, "DNA Microarrays: A Molecular Cloning Manual," Cold Spring Harbor Laboratory Press; 1st edition (Sep. 15, 2002). In some embodiments, the solid support is a microbead.

4. Methods of Diagnosis a. Obtaining a Biological Sample

The present diagnostic methods are useful for identifying whether a canine is genetically predisposed to suffer from skeletal dysplasia (SD) and/or intervertebral disc disease (IVDD) by determining the presence or absence of a retrogene insertion encoding canine fibroblast growth factor 4 (FGF4) on canine chromosome 12. The methods can involve obtaining a biological sample from a canine suspected of being genetically predisposed to suffer from skeletal dysplasia (SD) and/or intervertebral disc disease (IVDD).

The biological sample suitable for testing by the methods described herein comprises a template nucleic acid, e.g., genomic DNA. The biological sample can include body fluids including whole blood, serum, plasma, cerebrospinal fluid, urine, lymph fluids, semen, and various external secretions of the respiratory, intestinal and genitourinary tracts, tears, saliva, milk, white blood cells, myelomas, and the like; and biological fluids such as cell extracts, cell culture supernatants; fixed tissue specimens; and fixed cell specimens. Biological samples can also be from solid tissue, including hair bulb, skin, muscle, biopsy or autopsy samples or frozen sections taken for histologic purposes. These samples are well known in the art. A biological sample is obtained from any canine to be tested for retrogene insertion encoding canine fibroblast growth factor 4 (FGF4) on canine chromosome 12 as described herein. In some embodiments, the canine has lineage of a breed having a predisposition to chondrodystrophy (e.g., a chondrodystrophic (CD) breed, e.g., as reviewed in Smolders, et al., *Vet J*. 2013 March; 195(3):292-9). Illustrative chondrodystrophic (CD) dog breeds include without limitation, e.g., American Cocker Spaniel, Basset Hound, Beagle, Cardigan Welsh Corgi, Chesapeake Bay Retriever, Chihuahua, Coton de Tulear, Dachshund, English Springer Spaniel, French Bulldog, Jack Russell Terrier, Miniature Schnauzer, Nova Scotia Duck Tolling Retriever, Pekingese, Pembroke Welsh Corgi, Poodle, Portuguese Water Dog, Scottish Terrier, and Shih Tzu. A biological sample can be suspended or dissolved in liquid materials such as buffers, extractants, solvents and the like.

The biological sample may be obtained from a canine exhibiting symptoms of skeletal dysplasia (SD), chondrodystrophy and/or intervertebral disc disease (IVDD). In some embodiments, the canine is asymptomatic, but is suspected of being predisposed to developing skeletal dysplasia (SD), chondrodystrophy and/or intervertebral disc disease (IVDD), e.g., due to breed, parentage or lineage. In some embodiments, the biological sample is from a canine who has a parent, grandparent or sibling that is or has suffered from skeletal dysplasia (SD), chondrodystrophy and/or intervertebral disc disease (IVDD). In certain embodiments, a biological sample is also obtained from an canine is not suffering from or suspected of developing skeletal dysplasia (SD), chondrodystrophy and/or intervertebral disc disease (IVDD) as a negative control. In certain embodiments, a biological sample is also obtained from a canine known to be suffering from skeletal dysplasia (SD), chondrodystrophy and/or intervertebral disc disease (IVDD) as a positive control.

b. Detecting the Genotype

The retrogene insert encoding canine fibroblast growth factor 4 (FGF4) on canine chromosome 12 ("CAF12 FGF4 insert") can be detected using any methods known in art, including without limitation amplification, sequencing and hybridization techniques. Detection techniques for evaluating nucleic acids for the presence of a single base change involve procedures well known in the field of molecular genetics. Methods for amplifying nucleic acids find use in carrying out the present methods. Ample guidance for performing the methods is provided in the art. Exemplary references include manuals such as PCR Technology: PRINCIPLES AND APPLICATIONS FOR DNA AMPLIFICATION (ed. H. A. Erlich, Freeman Press, NY, N.Y., 1992); PCR PROTOCOLS: A GUIDE TO METHODS AND APPLICATIONS (eds. Innis, et al., Academic Press, San Diego, Calif., 1990); CURRENT PROTOCOLS IN MOLECULAR BIOLOGY, Ausubel, 1990-2017, including supplemental updates; Green and Sambrook, Molecular Cloning, A Laboratory Manual (4th Ed, 2012).

The nucleic acid template is isolated from the biological sample and a region of the CAF12 FGF4 insert (e.g., the 5'- or 3'-ends) is amplified using an oligonucleotide pair to form nucleic acid amplification products of all or part of the CAF12 FGF4 insert, generally also including flanking or abutting sequences of canine chromosome 12. Amplification can be by any of a number of methods known to those skilled in the art including PCR, and the methods are intended to encompass any suitable techniques of DNA amplification. A number of DNA amplification techniques are suitable for use with the present methods. Conveniently such amplification techniques include methods such as polymerase chain reaction (PCR), strand displacement amplification (SDA), nucleic acid sequence based amplification (NASBA), rolling circle amplification, T7 polymerase mediated amplification, T3 polymerase mediated amplification and SP6 polymerase mediated amplification. The precise method of DNA amplification is not intended to be limiting, and other methods not listed here will be apparent to those skilled in the art and their use is within the scope of the invention.

In some embodiments, the polymerase chain reaction (PCR) process is used (see, e.g., U.S. Pat. Nos. 4,683,195 and 4,683,202. PCR involves the use of a thermostable DNA polymerase, known sequences as primers, and heating cycles, which separate the replicating deoxyribonucleic acid (DNA), strands and exponentially amplify a gene of interest. Any type of PCR, including quantitative PCR, RT-PCR, hot start PCR, LA-PCR, multiplex PCR, touchdown PCR, finds use. In some embodiments, real-time PCR is used.

The amplification products are then analyzed in order to detect the presence or absence of the CAF12 FGF4 insert that is associated with canine skeletal dysplasia (SD) and/or intervertebral disc disease (IVDD), as discussed herein. By practicing the methods of the present methods and analyzing the amplification products it is possible to determine the genotype of individual canines with respect to the CAF12 FGF4 insert.

In some embodiments, analysis may be made by restriction fragment length polymorphism (RFLP) analysis of a PCR amplicon produced by amplification of genomic DNA with the oligonucleotide pair. In order to simplify detection of the amplification products and the restriction fragments, those of skill will appreciate that the amplified DNA will further comprise labeled moieties to permit detection of relatively small amounts of product. A variety of moieties are well known to those skilled in the art and include such labeling tags as fluorescent, bioluminescent, chemiluminescent, and radioactive or colorigenic moieties.

A variety of methods of detecting the presence and restriction digestion properties of CAF12 FGF4 insert amplification products are also suitable for use with the present methods. These can include methods such as gel electrophoresis, mass spectroscopy or the like. The present methods are also adapted to the use of single stranded DNA detection techniques such as fluorescence resonance energy transfer (FRET). For FRET analysis, hybridization anchor and detection probes may be used to hybridize to the amplification products. The probes sequences are selected such that in the presence of the SNP, for example, the resulting hybridization complex is more stable than if there is a G or C residue at a particular nucleotide position. By adjusting the hybridization conditions, it is therefore possible to distinguish between animals with the SNP and those without. A variety of parameters well known to those skilled in the art can be used to affect the ability of a hybridization complex to form. These include changes in temperature, ionic concentration, or the inclusion of chemical constituents like formamide that decrease complex stability. It is further possible to distinguish animals heterozygous for the SNP versus those that are homozygous for the same. The method of FRET analysis is well known to the art, and the conditions under which the presence or absence of the SNP would be detected by FRET are readily determinable.

Suitable sequence methods of detection also include e.g., dideoxy sequencing-based methods and Maxam and Gilbert sequence (see, e.g., Green and Sambrook, supra). Suitable HPLC-based analyses include, e.g., denaturing HPLC (dHPLC) as described in e.g., Premstaller and Oefner, LC-GC Europe 1-9 (July 2002); Bennet et al., BMC Genetics 2:17 (2001); Schrimi et al., Biotechniques 28(4):740 (2000); and Nairz et al., PNAS USA 99(16):10575-10580 (2002); and ion-pair reversed phase HPLC-electrospray ionization mass spectrometry (ICEMS) as described in e.g., Oberacher et al.; Hum. Mutat. 21(1):86 (2003). Other methods for characterizing retrogene inserts include, e.g., single base extensions (see, e.g., Kobayashi et al, Mol. Cell. Probes, 9:175-182, 1995); single-strand conformation polymorphism analysis, as described, e.g, in Orita et al., Proc. Nat. Acad. Sci. 86, 2766-2770 (1989), allele specific oligonucleotide hybridization (ASO) (e.g., Stoneking et al., Am. J. Hum. Genet. 48:70-382, 1991; Saiki et al., Nature 324, 163-166, 1986; EP 235,726; and WO 89/11548); and sequence-specific amplification or primer extension methods as described in, for example, WO 93/22456; U.S. Pat. Nos. 5,137,806; 5,595,890; 5,639,611; and 4,851,331; 5'-nuclease assays, as described in U.S. Pat. Nos. 5,210,015; 5,487,972; and 5,804,375; and Holland et al., 1988, Proc. Natl. Acad. Sci. USA 88:7276-7280.

Methods for detecting single base changes well known in the art often entail one of several general protocols: hybridization using sequence-specific oligonucleotides, primer extension, sequence-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and scoring by real-time pyrophosphate sequences. Analysis of amplified sequences can be performed using various technologies such as microchips, fluorescence polarization assays, and matrix-assisted laser desorption ionization (MALDI) mass spectrometry. In addition to these frequently used methodologies for analysis of nucleic acid samples to detect single base changes, any method known in the art can be used to detect the presence of the CAF12 FGF4 insert described herein.

For example FRET analysis can be used as a method of detection. Conveniently, hybridization probes comprising an anchor and detection probe, the design of which art is well known to those skilled in the art of FRET analysis, are labeled with a detectable moiety, and then under suitable conditions are hybridized a CAF12 FGF4 insert amplification product containing the site of interest in order to form a hybridization complex. A variety of parameters well known to those skilled in the art can be used to affect the ability of a hybridization complex to form. These include changes in temperature, ionic concentration, or the inclusion of chemical constituents like formamide that decrease complex stability. The presence or absence of the CAF12 FGF4 insert is then determined by the stability of the hybridization complex. The parameters affecting hybridization and FRET analysis are well known to those skilled in the art. The amplification products and hybridization probes described herein are suitable for use with FRET analysis.

In one embodiment, the CAF12 FGF4 insert is detecting using one or more oligonucleotide pairs configured or designed to detect the 5'-end and/or the 3'-end of the retrogene insertion. In some embodiments, the one or more oligonucleotide pairs are configured or designed or constructed to detect the 5' end of the retrogene insertion located at nucleic acid residue 1002 of SEQ ID NO:1. In some embodiments, an oligonucleotide in the one or more oligonucleotide pairs hybridizes to a sequence segment within nucleic acid residues 1-1001 of SEQ ID NO:1. In some embodiments, the one or more oligonucleotide pairs are configured to detect the 3'-end of the retrogene insertion located at nucleic acid residue 1000 of SEQ ID NO:2. In some embodiments, an oligonucleotide in the one or more oligonucleotide pairs hybridizes to a sequence segment within nucleic acid residues 1001-2000 of SEQ ID NO:2. In some embodiments, the one or more oligonucleotide pairs comprise one or more forward primers selected from the group consisting of: ACAGCTGGCATGGTCAGTTA (SEQ ID NO:13), GTGTTTGCATGGAGGAAGGT (SEQ ID NO:3), CTGAGCAAGAACGGGAAGAC (SEQ ID NO:4), AGCCTGATGGCTGGACTGTA (SEQ ID NO:5) and GTCCGTGCGGTGAAATAAAA (SEQ ID NO:6) and one or more reverse primers selected from the group consisting of TGCTGTAGATTTTGAGGTGTCTT (SEQ ID NO:7), CCTGATTTTGAGACAGCCAAA (SEQ ID NO:8), TTGATGCCCAGGAGGTAGTC (SEQ ID NO:9) and TGAGTGGGTTAAGGGTTTCG (SEQ ID NO:10). In some embodiments, the one or more oligonucleotides comprise one or more forward primers selected from the group consisting of: ACAGCTGGCATGGTCAGTTA (SEQ ID NO:13) and GTCCGTGCGGTGAAATAAAA (SEQ ID NO:6) and reverse primer TGCTGTAGATTTT-GAGGTGTCTT (SEQ ID NO:7).

c. Identifying or Selecting the Canine Based on Genotype

The methods identify individual canines based on the knowledge of the presence or absence of a retrogene insertion encoding canine fibroblast growth factor 4 (FGF4) on chromosome 12. Presence of the CAF12 FGF4 insert is statistically correlated with a predisposition to develop canine skeletal dysplasia (SD) and/or intervertebral disc disease (IVDD) in comparison to a canine that does not have the CAF12 FGF4 insert.

With the knowledge of the canine's genotype with respect to the CAF12 FGF4 insert, one can then identify and sort canines into groups of like phenotype(s), or otherwise use the knowledge of the genotype in order to predict which canines will have the desired phenotypes, for example, decreased susceptibility to develop SD and/or IVDD. Knowledge of the canine's genotype with respect to the CAF12 FGF4 insert allows a breeder to encourage breeding between canines with a desired CAF12 FGF4 genotype (e.g., where the CAF12 FGF4 insert is absent), and to discourage breeding between canines with an undesirable CAF12 FGF4 genotype (e.g., where the CAF12 FGF4 insert is present).

Selecting or sorting can be taken to mean placing canines in physical groupings such as pens, so that canines of like genotype are kept separate from canines of a different genotype. This would be a useful practice in the case of breeding programs where it would be desirable to produce canines of particular genotypes. For example, it may be desirable to breed canines that do not have the CAF12 FGF4 insert, such that breeding among these canines would only produce canines with a desired genotype with respect to the CAF12 FGF4 insert. On the other hand, it may also be desirable to decrease production of animals with an undesired CAF12 FGF4 insert genotype. Separating out canines with the desired CAF12 FGF4 insert genotype(s) would prevent canines with an undesired CAF12 FGF4 insert genotype from breeding with canines possessing a desired CAF12 FGF4 insert genotype, facilitating the reproduction of canines with an increased susceptibility to develop SD and/or IVDD, which is associated with presence of the CAF12 FGF4 insert. Furthermore, ensuring that at least one canine in a breeding pair possesses desired CAF12 FGF4 insert genotype allows for the frequency of the desired CAF12 FGF4 insert genotype to be increased in the next, and subsequent generations.

Sorting may also be of a "virtual" nature, such that a canine's genotype is recorded either in a notebook or computer database. In this case, canines could then be selected based on their known genotype without the need for physical separation. This would allow one to select for canines of desired phenotype where physical separation is not required. For example, many canine breed registries perform parentage verification using a set of alleles each time a canine is registered.

5. Kits

Further provided are kits. In some embodiments, the kits comprise one or more oligonucleotide pairs configured or designed to detect the presence or absence of a retrogene insertion encoding canine fibroblast growth factor 4 (FGF4) on chromosome 12. In some embodiments, the oligonucleotide pairs detect the 5'-end and/or the 3'-end of the retrogene insertion. In some embodiments, the 5'-end of the retrogene insertion encoding canine fibroblast growth factor 4 (FGF4) comprises a nucleic acid sequence having at least 90% sequence identity, e.g., at least 91%, 92%, 93%, 94%, 95%, 96%, 97%, 98%, 99%, or 100% sequence identity, to nucleic acid residues 1002-2001 SEQ ID NO:1. In some embodiments, the one or more oligonucleotide pairs are configured to detect the 5'-end of the retrogene insertion located at nucleic acid residue 1002 of SEQ ID NO:1. In some embodiments, an oligonucleotide in the one or more oligonucleotide pairs hybridizes to a sequence segment within nucleic acid residues 1-1001 of SEQ ID NO:1. In some embodiments, the 3'-end of the retrogene insertion encoding canine fibroblast growth factor 4 (FGF4) comprises a nucleic acid sequence having at least 90% sequence identity, e.g., at least 91%, 92%, 93%, 94%, 95%, 96%, 97%, 98%, 99%, or 100% sequence identity, to nucleic acid residues 1-1000 SEQ ID NO:2. In some embodiments, the one or more oligonucleotide pairs are configured to detect the 3'-end of the retrogene insertion located at nucleic acid residue 1000 of SEQ ID NO:2. In some embodiments, an oligonucleotide in the one or more oligonucleotide pairs hybridizes to a sequence segment within nucleic acid residues 1001-2000 of SEQ ID NO:2. In some embodiments, the one or more oligonucleotide pairs comprise one or more forward primers selected from the group consisting of: ACAGCTGGCATGGTCAGTTA (SEQ ID NO: 13), GTGTTTGCATGGAGGAAGGT (SEQ ID NO:3), CTGAGCAAGAACGGGAAGAC (SEQ ID NO:4), AGCCTGATGGCTGGACTGTA (SEQ ID NO:5) and GTCCGTGCGGTGAAATAAAA (SEQ ID NO:6) and one or more reverse primers selected from the group consisting of TGCTGTAGATTTTGAGGTGTCTT (SEQ ID NO:7), CCTGATTTTGAGACAGCCAAA (SEQ ID NO:8), TTGATGCCCAGGAGGTAGTC (SEQ ID NO:9) and TGAGTGGGTTAAGGGTTTCG (SEQ ID NO:10). In addition, the kit can comprise appropriate buffers, salts and other reagents to facilitate amplification and/or detection reactions (e.g., primers, labels, secondary antibodies).

EXAMPLES

The following examples are offered to illustrate, but not to limit the claimed invention.

Example 1

FGF4 retrogene on CFA12 is responsible for chondrodystrophy and intervertebral disc disease in dogs Materials and Methods Phenotype and Sample Collection. Blood samples, height at the withers, thoracic limb radiographs, and pictures (when possible), were collected from privately owned NSDTRs affected with owner or veterinarian reported skeletal dysplasia (SD), as well as phenotypically "normal" dogs. Additionally, blood samples were collected from cases of type I intervertebral disc disease (IVDD) seen at the University of California, Davis School of Veterinary Medicine Teaching Hospital and privately owned NSDTRs. IVDD cases were defined by the presence of one or more mineralized thoracolumbar intervertebral discs (IVD), as confirmed by vertebral column radiographs and/or the presence of extruded calcified degenerative disc material at surgery or necropsy. DNA was extracted from EDTA whole blood samples using Gentra Puregene DNA purification extraction kit (Qiagen, Valencia, Calif.). Collection of canine samples was approved by the University of California, Davis Animal Care and Use Committee (protocol #18561).

Genome-wide Association Study (GWAS). Genome-wide single nucleotide polymorphism (SNP) genotyping was performed using the Illumina Canine HD 174,000 SNP array (Illumina, San Diego, Calif.) for 13 NSDTR SD cases and 15 NSDTR controls with no reported SD. SNPs were pruned from analysis if the minor allele frequency was <5% and the call rate <90%. Additionally, a separate GWAS was performed for 36 IVDD cases from 16 breeds and 31 controls with no reported IVDD from 14 breeds (number of dogs from each breed listed in Table 1). The SNPs were pruned from analysis if the minor allele frequency was <10% and the call rate <90%. Chi-square association analysis, Bonferroni adjustments, and genomic inflation calculations were performed in Plink (59).

TABLE 1

Number of dogs per breed used in across breed IVDD GWAS

| Breed | # of Dogs | Phenotype |
|---|---|---|
| Basset Hound | 1 | Case |
| Beagle | 1 | Case |
| Boston Terrier | 3 | Control |
| Brittany | 3 | Control |
| Bulldog | 1 | Control |
| Cardigan Welsh Corgi | 1 | Case |
| Chihuahua | 3 | Case |
| Collie | 2 | Control |
| Coton de Tulear | 12 | 6 Cases, 6 Controls |
| Dachshund | 4 | Case |
| Dalmatian | 1 | Control |
| French Bulldog | 3 | Case |
| Ibizan Hound | 2 | Control |
| Jack Russell Terrier | 1 | Control |
| Lacy Dog | 1 | Control |
| Maltese | 1 | Case |
| Miniature Poodle | 1 | Case |
| Mix | 15 | 11 Cases, 4 Controls |
| NSDTR | 1 | Case |
| Pembroke Welsh Corgi | 1 | Case |
| Poodle | 1 | Control |
| Rottweiler | 1 | Case |
| Shetland Sheepdog | 2 | Control |
| Shih Tzu | 1 | Case |
| Whippet | 3 | Control |
| Yorkshire Terrier | 1 | Control |

Whole Genome Sequencing (WGS). For library prep and sequencing, DNA was fragmented using the Covaris E220 sonicator (Covaris Inc.), and then followed by selection of 550 bp insert size fragments. Illumina paired-end 150 bp libraries were prepared using PCR-free library prep kits. Sequencing was done on the HiSeq2500 platform at the BGI sequencing facility. Reads were scanned for sequencing adaptors and low quality sequences using the Trimmomatic software package (V 0.36) 60. High quality reads were aligned to the dog reference genome canFam3 (61) using the BWA-MEM algorithm of the BWA software package (v0.7.7) (62). Duplicate reads were excluded using Picard v2.2.4 tool MarkDuplicates (63). Variant calling was performed using GATK HaplotypeCaller (v3.5) (64). SNPs and small insertions and deletions (indels) were investigated for segregation with the IVDD phenotype in a 4 Mb region (chr12:33.1-35.5 Mb (canFam3)), which included the critical interval identified using GWAS. Segregation of variants was performed using 2 cases (1 affected NSDTR and 1 Dachshund) compared to 83 controls of various normal legged breeds. To investigate the presence of large indels within the critical interval, BAM files covering the associated interval were scanned by eye using the Integrative Genomics Viewer (IGV, Broad Institute) in 2 cases (1 Dachshund and 1 SD affected NSDTR) and 2 controls (1 NSDTR and 1 Saluki) for segregation with the IVDD phenotype. The reads were viewed as color-coded by insert size and pair orientation to flag mate pairs that mapped to other chromosomes in order to easily identify large insertions and deletions.

Investigation of Large Indels. BAM files for additional control genomes (1 NSDTR, 1 Weimaraner, 1 Border Collie (ncbi.nlm.nih.gov/biosample/SAMN03801652)) were used to evaluate segregation of the 8 identified large indels. The remaining segregating large indels (Deletions 1-3 and Insert 5) were investigated in additional cases and controls using PCR (primers listed in Table 2).

TABLE 2

Primers used to large indels identified CFA12: 33.1-35.5 Mb (canFam3)

| | Forward Primer (5'→3') | Reverse Primer (5'→3') |
|---|---|---|
| CFA7 Insert | CTCTGTGGACCTCTTTCAACG (SEQ ID NO: 15) | TGACACCAGTGAGAATTGCAT (SEQ ID NO: 20) |

TABLE 2-continued

Primers used to large indels identified CFA12: 33.1-35.5 Mb (canFam3)

| | Forward Primer (5'→3') | Reverse Primer (5'→3') |
|---|---|---|
| Deletion 1 | TGCTTGCTCCAGCTCTGTTA (SEQ ID NO: 16) | TTGGCCATAATTTTCCTTGG (SEQ ID NO: 21) |
| Deletion 2 | AAATGGCATATGGGCTGAGT (SEQ ID NO: 17) | TCTGCAAAACAGCTTGCATT (SEQ ID NO: 22) |
| Deletion 3 | CACTGTTGGCAGTCCTCAAA (SEQ ID NO: 18) | AAAGCCGGTTGTTGATGAAG (SEQ ID NO: 23) |
| Insert 5 | ATGCTACACCACTCCCTGCT (SEQ ID NO: 19) | ATCCTTGCCAAAACTGATGG (SEQ ID NO: 24) |

Investigation of potential insert from CFA 7. The integrity of the region on CFA7 (approximately chr7:68,371,500-68,374,000) was tested using PCR and sequencing, as read mates at the FGF4 insertion site on CFA12 also mapped to this location. Primers (listed in Table 2) spanning the potentially inserted segment of CFA7 were used in PCR for 6 cases (1 NSDTR, 1 Beagle, 1 Basset Hound, 1 French Bulldog, and 1 Maltese) and 1 control (Boston Terrier) using the LongAmp Taq PCR Kit (New England Biolabs, Ipswich, Mass., USA). If the genome assembly is correct, PCR product size should be 2,077 bp, if not, the product would only be 842 bp. PCR products for 3 cases and 1 control were sequenced on an Applied Biosystems 3500 Genetic Analyzer using the Big Dye Terminator Sequencing Kit (Life Technologies, Burlington, ON, Canada) and the products aligned to the UCSC genome browser using BLAT (genome.ucsc.edu/).

Cloning. To obtain the full FGF4 retrogene insertion sequence on CFA12, as well as on CFA18 for comparison, the PCR products using CFA12 FGF4 Insertion and CFA18 FGF4 Insertion primer pairs (Table 3), respectively, were cloned using the TOPO TA Cloning kit with PCR2.1 TOPO (Thermo Fisher Scientific, Inc., Waltham, Mass., USA) and One Shot TOP10 competent cells. CFA12 and 18 FGF4 insertions were amplified from genomic DNA using the LongAmp Taq PCR Kit (New England Biolabs, Ipswich, Mass., USA) using primers flanking the inserts on CFA12 and 18, respectively and recommended cycling conditions. The CFA12 FGF4 insertion was cloned from a Beagle and the CFA18 FGF4 insertion was cloned from a Dachshund. Plasmid DNA was extracted using the QIAprep Spin Miniprep Kit (Qiagen, Valencia, Calif., USA). To confirm successful transformation, plasmid DNA was sequenced using vector primers M13.F and M13.R (Thermo Fisher Scientific, Inc., Waltham, Mass., USA) on an Applied Biosystems 3500 Genetic Analyzer using the Big Dye Terminator Sequencing Kit (Life Technologies, Burlington, ON, Canada) and analyzed using VectorNTI software (Thermo Fisher Scientific, Inc., Waltham, Mass., USA). Internal FGF4 primers were also used to create overlapping contigs and ensure the entire insert was sequenced (listed in Table 3). CFA12 and 18 FGF4 inserts were aligned to endogenous FGF4 sequence to confirm presence of the gene's entire coding sequence. Polymorphisms identified were not queried in additional dogs, so could be due to sequencing or cloning error or be dog/breed specific.

TABLE 3

Primers used to sequence and assay the FGF4 insert on CFA12 and 18

| | Forward Primer (5'→3') | Reverse Primer (5'→3') |
|---|---|---|
| CFA12 FGF4 Insertion | ACAGCTGGCATGGTCAGTTA (SEQ ID NO: 13) | CCTGATTTTGAGACAGCCAAA (SEQ ID NO: 8) |
| CFA18 FGF4 Insertion | TTGGGAATGTCAAACCACTG (SEQ ID NO: 25) | AGGGCCAAGTGTCCAATACA (SEQ ID NO: 28) |
| FGF4.F1 | GTGTTTGCATGGAGGAAGGT (SEQ ID NO: 3) | |
| FGF4.F2 | CTGAGCAAGAACGGGAAGAC (SEQ ID NO: 4) | |
| FGF4.F3 | AGCCTGATGGCTGGACTGTA (SEQ ID NO: 5) | |
| FGF4.F4 | GTCCGTGCGGTGAAATAAAA (SEQ ID NO: 6) | |
| FGF4.R1 | | TTGATGCCCAGGAGGTAGTC (SEQ ID NO: 9) |
| FGF4.R2 | | TGAGTGGGTTAAGGGTTTCG (SEQ ID NO: 10) |

TABLE 3-continued

Primers used to sequence and assay the FGF4 insert on CFA12 and 18

| | Forward Primer (5'→3') Reverse Primer (5'→3') |
|---|---|
| FGF4_TSS.F1 | GCGCTCCGCACCGAGTCC (SEQ ID NO: 26) |
| FGF4_TSS.F2 | CTCCATGCAGCCCGGGTA (SEQ ID NO: 27) |

Transcription start site (TSS) Investigation. To ensure the CFA12 FGF4 insertion included the transcription start site (TSS), PCR was performed using cDNA with primers at varying positions 5' to the FGF4 start codon (Table 3). cDNA was synthesized from RNA extracted from neonatal intervertebral disc (IVD) and vertebral body (VB), as described below, from a Beagle. Amplified products were visualized on a 2% agarose gel.

Genotyping Assay. The presence or absence of the FGF4 insertion on CFA12 and 18 was assayed using a PCR-based genotyping test. Three primer PCR was performed using a forward and reverse primer flanking the respective insert, as well an additional forward primer located within the FGF4 insert (listed in Table 4). For the CFA12 FGF4 insert assay, each reaction included 12 µl water, 2 µl 10× Buffer, 0.8 µl 25 mM MgCl$_2$, 2 µl dNTP, 0.5 µl of the external forward primer (20 µM), 0.7 µl of the internal forward primer (20 µM), 0.8 µl of the reverse primer (20 µM), 0.2 µl of HotStarTaq DNA Polymerase (Qiagen, Valenica, Calif., USA), and 1 µl of DNA. For the CFA18 FGF4 insert assay, each reaction included 12 µl water, 2 µl 10× Buffer, 0.8 µl 25 mM MgCl$_2$, 2 µl dNTP, 0.5 µl of the external forward primer (20 µM), 0.6 µl of the internal forward primer (20 µM), 0.9 µl of the reverse primer (20 µM), 0.2 µl of HotStarTaq DNA Polymerase (Qiagen, Valenica, Calif., USA), and 1 µl of DNA. Amplified products were visualized on a 2% agarose gel. For the CFA18 FGF4 insertion: wild type dogs had a single 388 bp band, homozygous mutant samples had a single 168 bp band, and both bands were present in heterozygous samples. For the CFA12 FGF4 insertion, a single 333 bp band was present in wild type samples, a single 654 bp band was present in the homozygous mutant samples, and both bands were present in heterozygous samples.

TABLE 4

| | External Forward Primer (5'→3') | Internal Forward Primer (5'→3') | External Reverse Primer (5'→3') |
|---|---|---|---|
| CFA12 FGF4 Insert Genotyping Assay | ACAGCTGGCAT GGTCAGTTA (SEQ ID NO: 13) | GTCCGTGCGGTGA AATAAAA (SEQ ID NO: 6) | TGCTGTAGATTTTG AGGTGTCTT (SEQ ID NO: 7) |
| CFA18 FGF4 Insert Genotyping Assay | TTGGGAATGTC AAACCACTG (SEQ ID NO: 25) | GTCCGTGCGGTGA AATAAAA (SEQ ID NO: 6) | GTTCCCTCCATTTC GGTTT (SEQ ID NO: 29) |

Height at the withers was collected for 20 male NSDTRs to associate dog height with the CFA12 FGF4 insertion. Significance was determined using a one-tailed T-test and a threshold cutoff of p<0.05.

To compare the significance of association of the CFA12 FGF4 insertion to the most highly associated SNP and the CFA18 FGF4 insertion, 34 of 36 IVDD cases and 31 controls were genotyped for both the CFA12 and CFA18 FGF4 insertions. Chi square and odds ratio analysis was performed in Plink (59)

IVDD Incidence Across Breeds seen at UC Davis SVM VMTH. To assess frequency of IVDD in specific breeds, UC Davis School of Veterinary Medicine Teaching Hospital (VMTH) records were searched between 1980 and 2016 for dogs with a clinical diagnosis of "disc/k disease" or "IVDD." Significantly over or underrepresented breeds relative to the total VMTH hospital population were determined based on a Chi-squared test. Significance was set at p<0.05.

qRT-PCR. cDNA was prepared from RNA that was extracted from IVD or VB dissected from neonatal canine tail samples, skeletal muscle, and testis, using the QuantiTect Reverse Transcription Kit (Qiagen, Valencia, Calif., USA) and the RNeasy Fibrous Tissue Mini Kit (Qiagen, Valencia, Calif., USA), respectively. Additionally, cDNA was made from commercially available Beagle skeletal muscle and testis RNA (Zyagen, San Diego, Calif., USA).

Semi-quantitative RT-PCR was performed for genes within and near the critical interval, including COL9A1, SMAP1, B3GAT2, OGFRL1, LINC00472, RIMS1, KCNQ5, and COL12A1, as well as FGF4, for VB, IVD, skeletal muscle, and testis cDNA from a case and control. RPS5 was also included as a housekeeping gene control. All case samples were collected from a Beagle, while control VB and IVD were from a Cane Corso and skeletal muscle and testis from a Labrador Retriever. Primers spanning at least 1 intron were designed for all genes using Primer3, except for RPS5 in which the primers were as recommended by Brinkhof et al. (65,66). Each reaction included 13.9 µl water, 2 µl 10× Buffer with MgCl$_2$, 1 µl dNTP, 1 µl of each forward and reverse primers (20 µM) (listed in Table 5), 1 µl of HotStarTaq DNA Polymerase (Qiagen, Valenica, Calif., USA), and 1 µl of cDNA made from 1000 ng of RNA. Amplified products were visualized on a 2% agarose gel.

TABLE 5

Primers used for semi-qPCR and qRT-PCR experiments

| | Forward Primer (5'→3') | Reverse Primer (5'→3') |
|---|---|---|
| COL9A1 | TTCTGTCGGACCAAGAGGAC (SEQ ID NO: 30) | CCATCATGAAAGCCAATGGT (SEQ ID NO: 40) |
| SMAP1 | AGGCTCAGAAGCTGAACAGA (SEQ ID NO: 31) | TCTGGTGTCCATTGGTCTAG G (SEQ ID NO: 41) |
| B3GAT2 | CCTACAGCCTGGAGCTGTTC (SEQ ID NO: 32) | GGCTTTTGGATTGGACAAGA (SEQ ID NO: 42) |

TABLE 5-continued

Primers used for semi-qPCR and qRT-PCR experiments

| | Forward Primer (5'→3') | Reverse Primer (5'→3') |
|---|---|---|
| OGFRL1 | AAGCAACTGCCAAACCAAAG (SEQ ID NO: 33) | GTTCTCTCAGGGGGAAAAGC (SEQ ID NO: 43) |
| LINC00472 | GGGCTGTACTGGCTCATTGT (SEQ ID NO: 34) | AGAGCAGCACACCCAAGTCT (SEQ ID NO: 44) |
| RIMS1 | TGGCCATCTCTGCTCCTACT (SEQ ID NO: 35) | ACCTCAGAACCAGCACCTGT (SEQ ID NO: 45) |
| KCNQ5 | TTGTGGAAAAGGATGCCAAT (SEQ ID NO: 36) | GGCGGTGCTGTTCTTGTACT (SEQ ID NO: 46) |
| COL12A1 | CTACAGGGGACGACAGAAGG (SEQ ID NO: 37) | CTGCTTCTGCTCTGGTGAGA (SEQ ID NO: 47) |
| FGF4 | GACTACCTCCTGGGCATCAA (SEQ ID NO: 38) | GTCTTCCCGTTCTTGCTCAG (SEQ ID NO: 48) |
| RPS5 | TCACTGGTGAGAACCCCCT (SEQ ID NO: 39) | CCTGATTCACACGGCGTAG (SEQ ID NO: 49) |

Quantitative RT-PCR was performed for FGF4 using cDNA synthesized from 500 ng of RNA extracted from IVD and VB dissected from the tails of 4 cases (4 Beagle) and 5 controls (1 Rottweiler and 4 Cane Corso). A 2-step cycle protocol was employed using the Rotor-Gene SYBR Green PCR Kit (Qiagen, Valencia, Calif., USA) on the Rotor Gene Q real-time PCR system: Initial denaturation at 95° C. for 5 minutes; Annealing at 95° C. for 5 seconds and extension at 60° C. for 10 seconds for 35 cycles; Final melt curve. Samples were run in triplicate with 20 ng of template cDNA each for both the IVD and VB experiment. FGF4 transcript levels were normalized to RPS5 and analyzed for fold change differences in expression using ΔΔCT. A technical replicate was removed from analysis if the standard deviation of the 3 technical replicates was greater than 1, and a sample was removed from analysis if there were less than 2 technical replicates that met this criteria. Fold change in expression of FGF4 in IVD and VB was calculated by taking $2^{-(\Delta\Delta CT)}$ for each tissue, respectively. Statistical significance was assessed using a Mann-Whitney-Wilcoxin test.

Results

A form of skeletal dysplasia (SD) is common in the NSDTR and is characterized by variable decrease in limb length and associated abnormalities including long bone bowing, physeal widening, and joint incongruity. (FIG. 1a, 1b). On physical examination, in addition to shorter limbs, SD dogs may also have valgus limb deformities and larger ears (pinnae). While SD is a common phenotype in the breed, the degree of severity is highly variable.

Figure 1C:
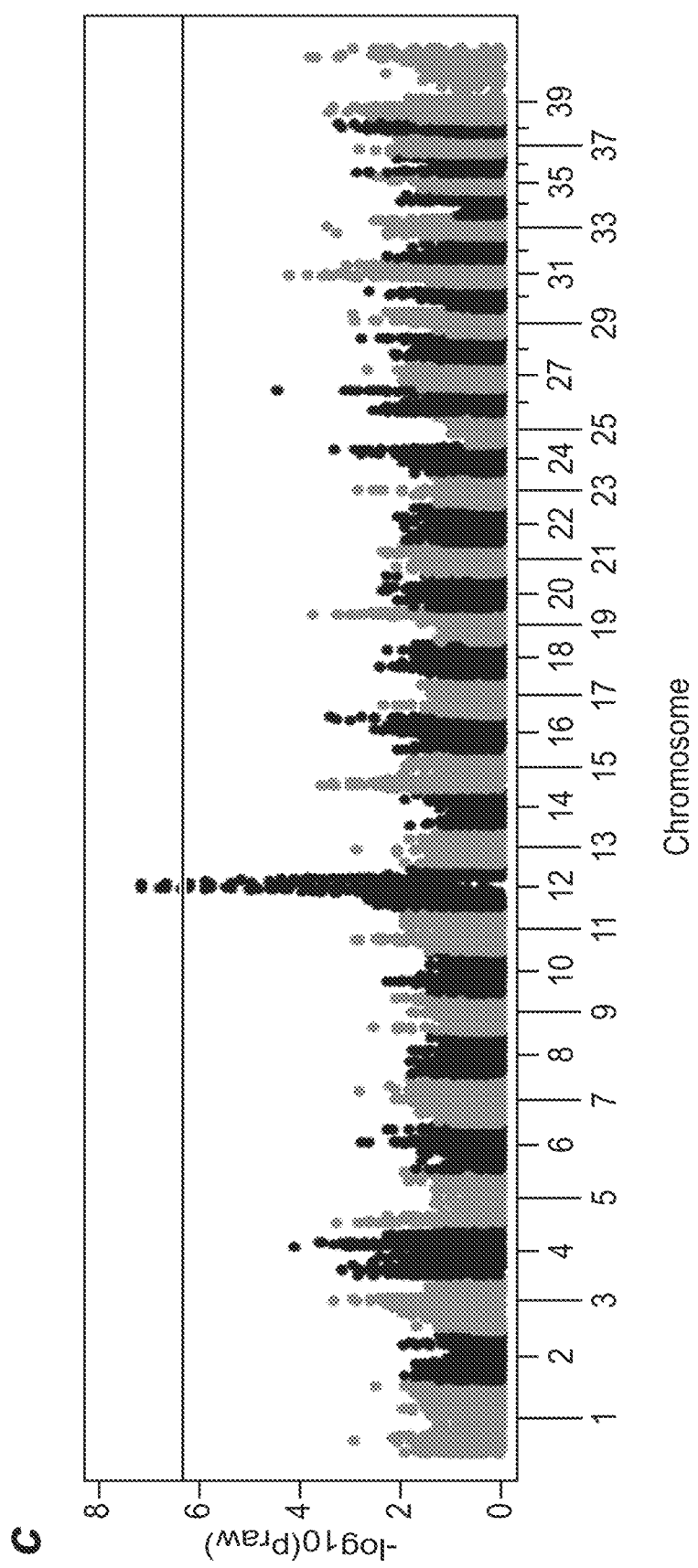
Figure 2:
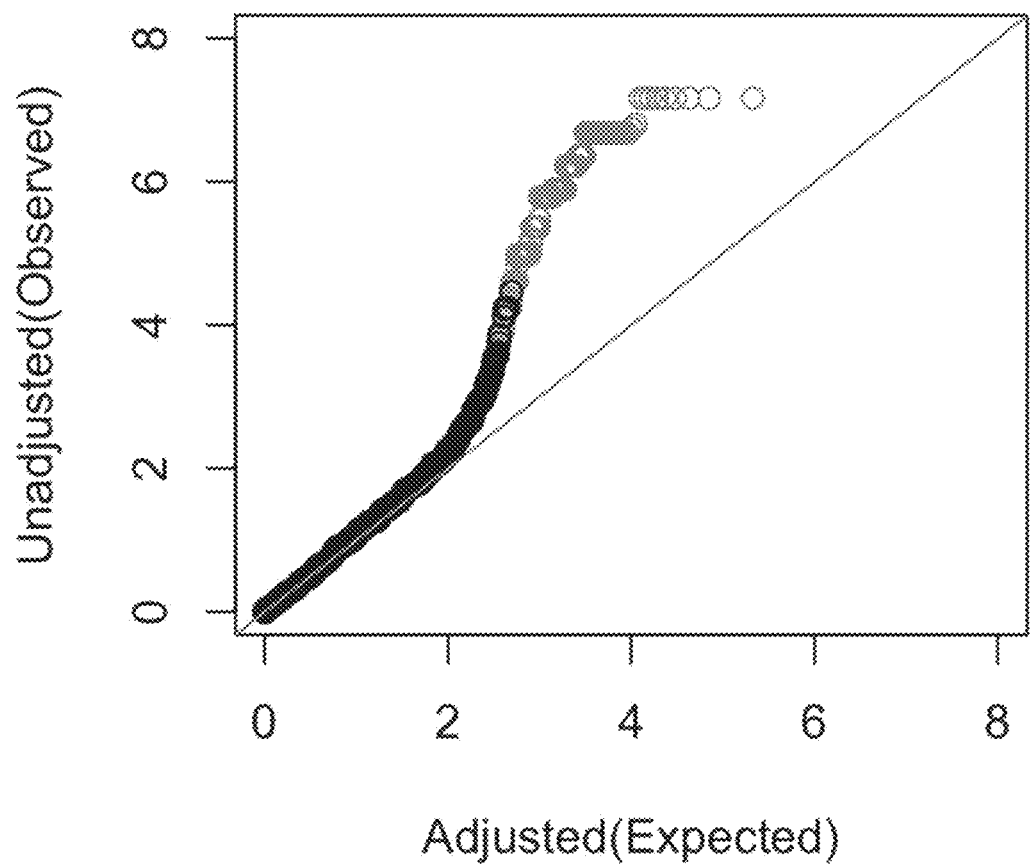
FIG. 2 illustrates quantile-quantile (QQ) plot shows −log 10 of the expected versus observed p-values plotted for each SNP, with the SNPs on CFA12 colored in grey.

To determine a region of the genome associated with SD in the NSDTR, genome-wide association analysis was performed using 13 NSDTR with severe SD and 15 NSDTR controls without severe SD. There were 41 SNPs that were genome-wide significant with a pBonferroni<0.05, all present between chr12:35,413,695-46,117,273 (top SNP-chr12: 36,790,324 pBonferroni=0.007232) (canFam2) (FIG. 1c, FIG. 2).

Underlying this strong association for SD in NSDTRs was an approximately 12 Mb critical interval from chr12:36-48 Mb (canFam2). Since the NSDTR SD phenotype is not uncommon in different dog breeds, we investigated haplotype sharing across breeds and observed that a portion of this associated haplotype was shared with two breeds of dog considered classically chondrodystrophic: the American Cocker Spaniel and Beagle (1,3). By plotting the minor allele frequency (MAF) across this interval for 7 American Cocker Spaniels, 14 Beagles, and 13 SD affected NSDTR, the critical interval identified via GWAS for SD was shortened to a shared haplotype from chr12:36.4-38.3 Mb (canFam2) (FIG. 3a). Interestingly, the breeds that shared this smaller haplotype have been well characterized as chondrodystrophic and predisposed to Hansen's type I IVDD, suggesting that the associated SD locus in the NSDTR may also be causing chondordystrophy across dog breeds.

Figure 3C:
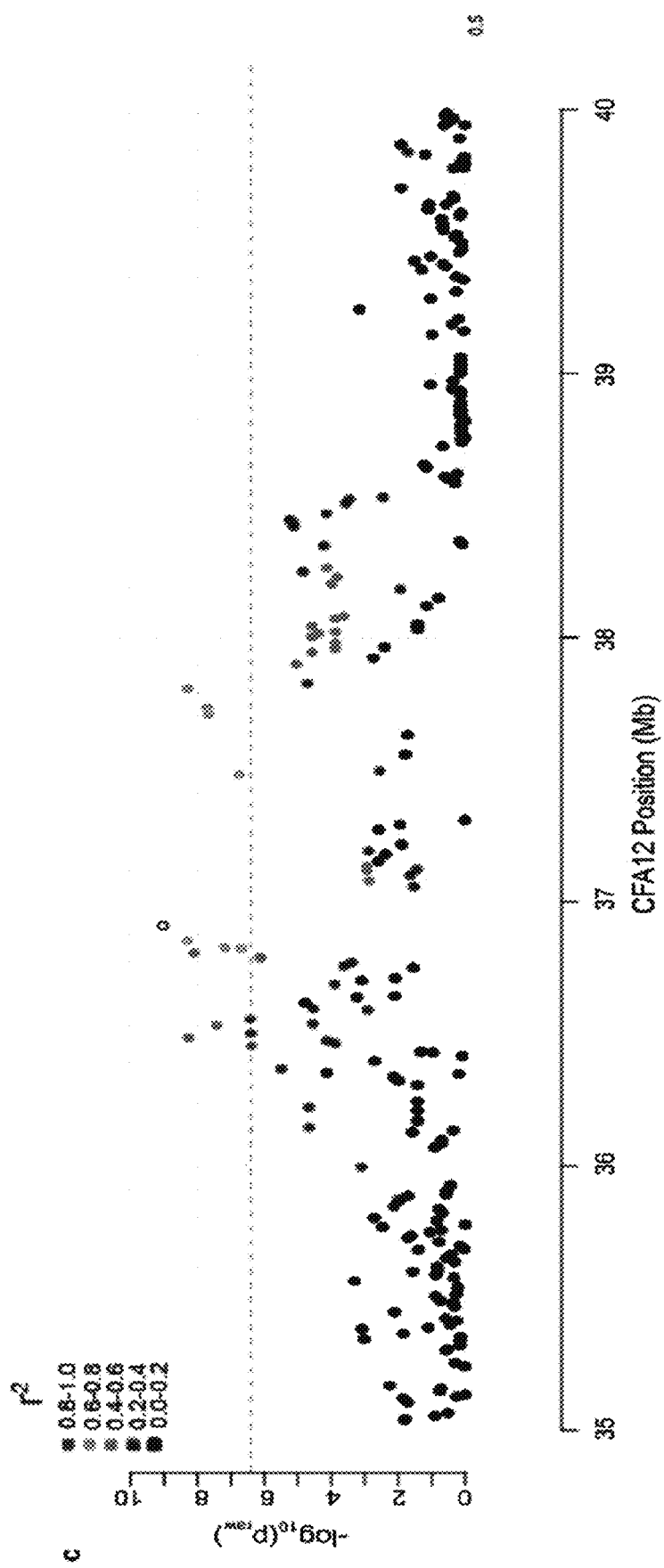

In order to test this hypothesis, a second genome-wide association study was performed using IVDD affected cases (n=36) and unaffected controls (n=31) across 26 dog breeds (Table 6). The most highly associated SNP was located on CFA12 (chr12:36,909,311 (canFam2)) with a $p_{raw}$=3.191× $10^{-15}$, pBonferroni=4.02×$10^{-10}$, and odds ratio of 32.67 (FIG. 3b). Observing LD with the highest associated SNP using $r^2$ values, the critical interval identified via GWAS for IVDD overlaps with that seen when mapping MAF across breeds (FIG. 3c).

TABLE 6

| Breed | VMTH Pop. % | IVDD % | Chi square | Significance | Increase or Decrease | CFA12 FGF4 Insert Allele Frequency |
|---|---|---|---|---|---|---|
| American Cocker Spaniel | 2.3 | 2.99 | 9.15 | 0.003 | Increase | 0.95 |
| Basset Hound | 0.51 | 1.24 | 45.21 | 1.77 × $10^{-11}$ | Increase | 0.68 |
| Beagle | 0.86 | 2.42 | 120.69 | 4.47 × $10^{-28}$ | Increase | 0.97 |
| Corgi | 0.67 | 1.82 | 85.41 | 2.43 × $10^{-20}$ | Increase | 0.82 |
| Dachshund | 2.68 | 25.95 | 8874.25 | <0.000001 | Increase | 0.98 |
| French Bulldog | 0.39 | 1.89 | 248.09 | 6.77 × $10^{-56}$ | Increase | 0.94 |
| Pekingese | 0.35 | 1.6 | 189.72 | 3.66 × $10^{-43}$ | Increase | 0.44 |
| Brittany | 0.49 | 0.24 | 5.34 | 0.021 | Decrease | 0.00 |
| Bulldog | 0.97 | 0.07 | 35.83 | 2.16 × $10^{-9}$ | Decrease | 0.00 |
| Cairn Terrier | 0.23 | 0.07 | 4.46 | 0.035 | Decrease | 0.00 |
| Scottish Terrier | 0.31 | 0.1 | 6.18 | 0.013 | Decrease | 0.05 |
| Shetland Sheepdog | 0.93 | 0.19 | 25.29 | 4.95 × $10^{-7}$ | Decrease | 0.00 |
| Springer Spaniel | 0.96 | 0.62 | 5.11 | 0.024 | Decrease | 0.11 |

TABLE 6-continued

| Breed | VMTH Pop. % | IVDD % | Chi square | Significance | Increase or Decrease | CFA12 FGF4 Insert Allele Frequency |
|---|---|---|---|---|---|---|
| West Highland White Terrier | 0.53 | 0.12 | 13.72 | 0.0002 | Decrease | 0.00 |
| Yorkshire Terrier | 1.56 | 0.96 | 10.13 | 0.002 | Decrease | 0.00 |

Investigation of IVDD in breeds seen at the UC Davis School of Veterinary Medicine Teaching Hospital: Canine cases seen at the UC Davis School of Veterinary Medicine Teaching Hospital between 1980 and 2016 were queried for a clinical diagnosis of "disc/k disease" or "IVDD." 203,958 cases were seen, of which 4,177 were diagnosed with "disc/k disease" or "IVDD." The breeds shown have a p-value associated with an increase or decrease in incidence of IVDD. Allele frequencies calculated from on dogs genotyped in Table 10, below.

To identify a causative variant for SD and IVDD, paired-end whole genome sequences of 2 cases, 1 SD affected NSDTR and 1 IVDD affected Dachshund, and 83 unaffected controls were investigated in the associated interval. There were 9,156 SNP variants and 7,877 insertion/deletion (indel) variants identified from chr12:33.1-35.5 Mb (canFam3) (chr12:36.1-38.5 Mb (canFam2)); however, none segregated with the IVDD phenotype. The same interval was also investigated by visual inspection of BAM files to flag mate pairs with unusual insert sizes in an effort to identify any large indels. Using the 2 cases and 2 controls, 8 large indels (>200 bp) were identified within the interval (Table 7). Four large indels did not segregate when investigated in additional control genomes, while the remaining 4 were eliminated after PCR showed lack of segregation between cases and controls.

TABLE 7

| Indel Coordinates (canFam3) | Indel | Method of Elimination |
|---|---|---|
| Chr12:33,927,660-33,928,003 | Deletion 1 | PCR |
| Chr12:34,256,430-34,256,530 | Deletion 2 | PCR |
| Chr12:34,467,000 | Insertion 1 | Additional Genomes |
| Chr12:34,734,000 | Insertion 2 | Additional Genomes |
| Chr12:34,758,000 | Insertion 3 | Additional Genomes |
| Chr12:34,947,000 | Insertion 4 | Additional Genomes |
| Chr12:35,228,600-35,228,800 | Deletion 3 | PCR |
| Chr12:35:498,000 | Insertion 5 | PCR |

Large indels identified via BAM file investigation: Coordinates and method of elimination for each of the 8 segregating large indels identified in 2 cases (1 Dachshund and 1 SD NSDTR) and 2 controls (1 NSDTR and 1 Saluki). Insertions 1-4 were eliminated based on lack of segregation with investigation of additional control genome BAM files. Deletions 1-3 and Insert 5 were eliminated based on lack of segregation demonstrated via PCR of additional cases and controls.

Figure 4:
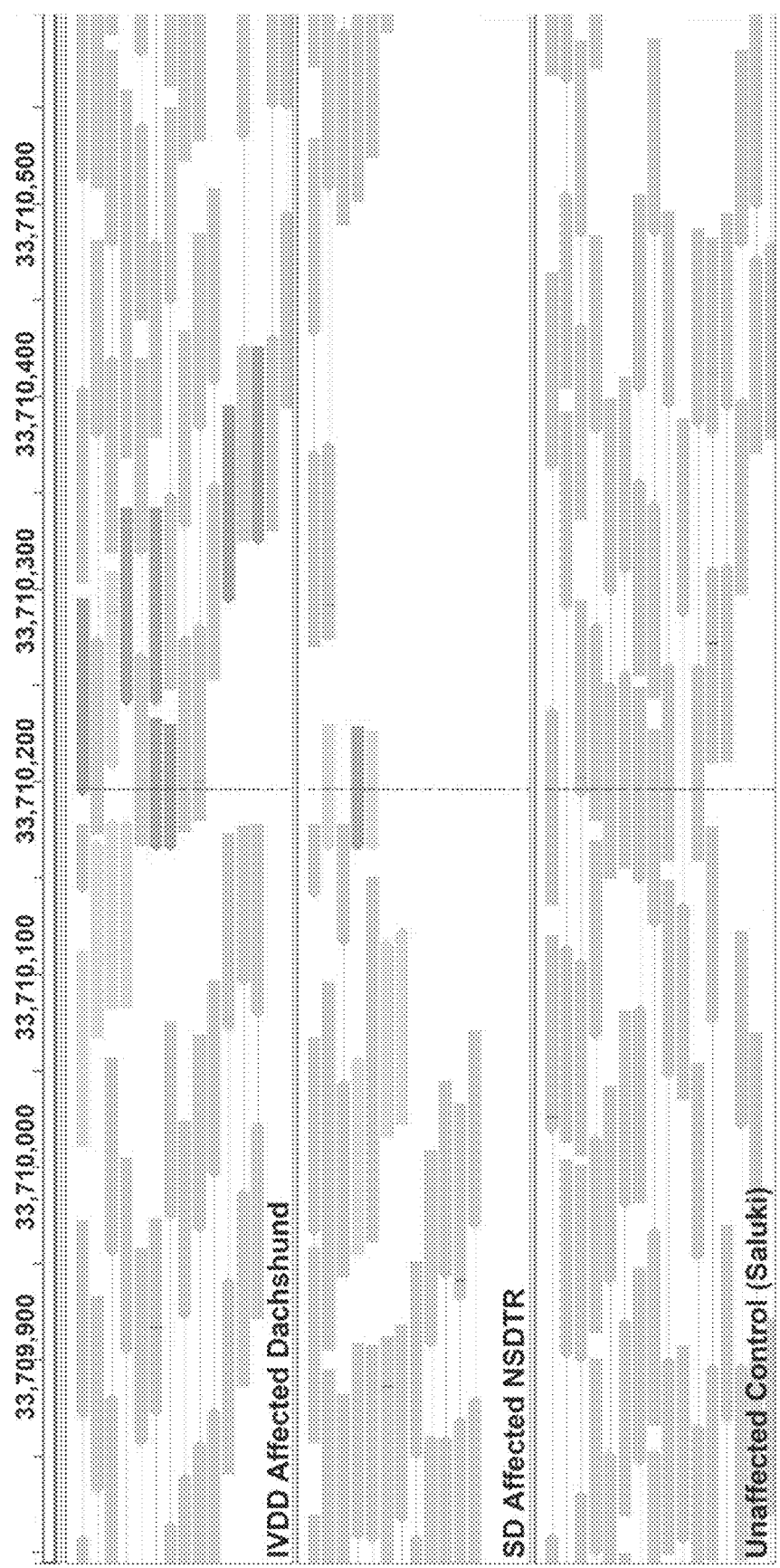
FIG. 4 illustrates large insertion identified on CFA12: Screenshot of the Integrative Genomics Viewer (IGV-Broad Institute) showing an insertion at approximately 12:33,710, 200 (canFam3) in an IVDD affected Dachshund case and a SD affected NSDTR that is not present in the Saluki unaffected control. Read mates in green map to chr18:48.4 Mb (canFam3) and the read mates in blue map to chr7:68.3 Mb (canFam3).

Visual inspection of the BAM files for read-pairs mapping to a different chromosome location identified a region, located at approximately chr12:33,710,200 (canFam3), that segregated with the 2 cases and 2 controls (FIG. 4). At this location, read mates mapped to chr18:48.4 Mb (canFam3) and chr7:68.3 Mb (canFam3) in the NSDTR and Dachshund cases, but none of the controls. The reads that mapped to CFA18 aligned to endogenous FGF4, which was highly suggestive of a FGF4 retrogene insertion at this location. The reads that mapped to CFA7 were investigated by PCR and appear to mark a genome assembly error or a mutation within the dog used for the genome assembly (canFam3).

Figure 5:
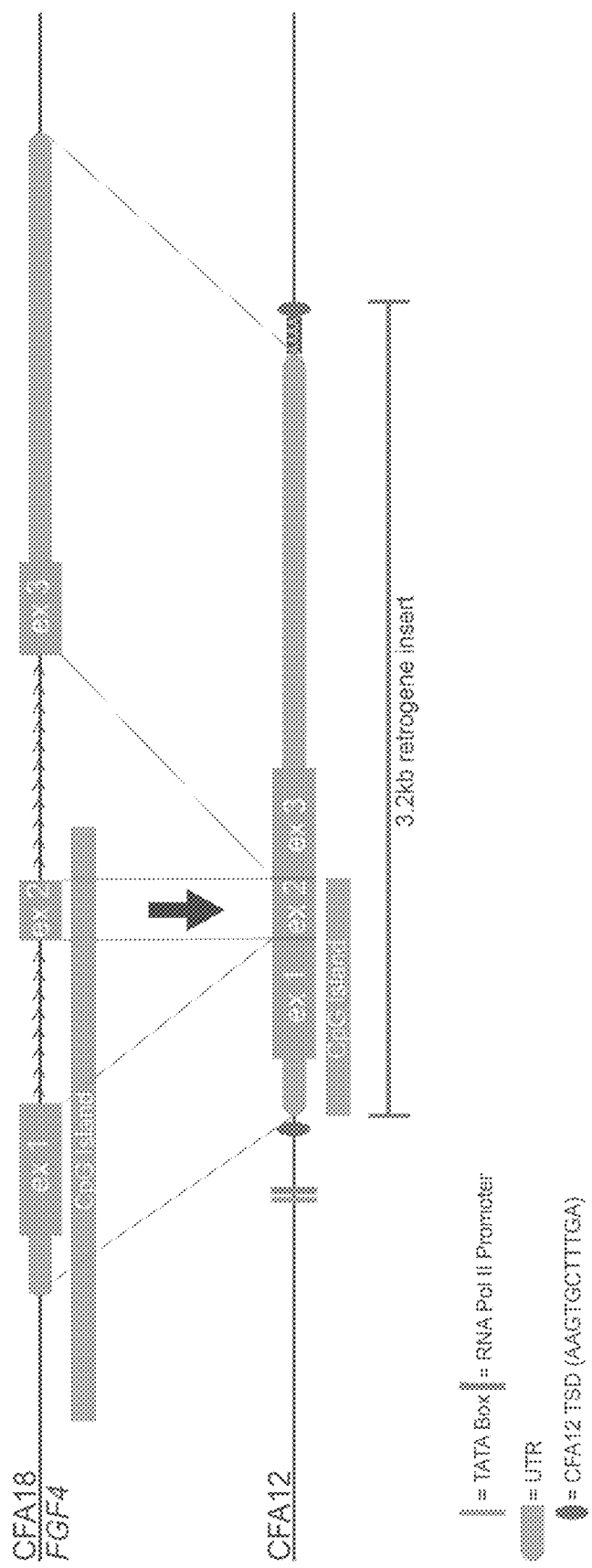
FIG. 5 illustrates a schematic of endogenous FGF4 (CFA18) retrotransposition to CFA12:33,710,178 (canFam3): Predicted TATA box at chr12:33,709,940-947 (canFam3) and predicted RNA Pol II promoter at chr12:33,709, 964-976 (canFam3), which are 239 bp and 215 bp upstream, respectively (38). Endogenous FGF4 untranslated regions (UTR) are unknown in the dog; however, they were approximated in the figure based on human and mouse TransMap data available at the UCSC genome browser (genome.ucsc.edu). The predicted 5'UTR spans from chr18:48,413, 185-48,413,480 (canFam3); however, RT-PCR in IVD from a Beagle suggest that the TSS is located between chr18:48, 413,315-48,413,402 (canFam3). The insert includes all predicted 3'UTR, followed by 42 adenine residues and the duplicated 11 bp TSD sequence (AAG TGC TTT GA; SEQ ID NO:14) (chr12:33,710,168-33,710,178 (canFam3)). Endogenous FGF4 sequence that was retrotransposed also includes a large CpG island.

To investigate the potential FGF4 insert on CFA12, the region was PCR amplified using primers flanking the insertion site in an IVDD affected Beagle. Wild type dogs without the insert had a single 615 bp band, while dogs homozygous for the CFA12 FGF4 insertion had an approximately 4 kb product. Sanger sequencing showed the insertion on CFA12 is 3,209 bp long (GenBank Accession #MF040221) and includes endogenous FGF4 cDNA (i.e. FGF4 exons spliced without introns), as shown in the insert schematic comparing endogenous FGF4 to the CFA12 insert (FIG. 5). The insert also contains a majority of the predicted 5'UTR, which includes the transcription start site (TSS) as only PCR primers FGF4_TSS.F1 and FGF4.R1 yielded a product in RT-PCR using cDNA from neonatal Beagle IVD (Table 2).

In order to compare the CFA12 FGF4 retrogene to the previously identified CFA18 FGF4 retrogene, it was necessary to obtain the full length sequence of the CFA18 insertion (26). The cloned product was sequenced using the flanking and common internal primers (Table 2), yielding a 2,665 bp insert (GenBank Accession #MF040222). While it contained the same length 5'UTR and FGF4 cDNA as that seen in the CFA12 FGF4 insert, the 3'UTR was shortened in comparison. The 3'UTR of the CFA18 FGF4 insert was followed by a sequence containing 30 adenine and 1 guanine residues and a different target site duplication (TSD) sequence (AAG TCA GAC AGA G (SEQ ID NO:50)).

Figure 6:
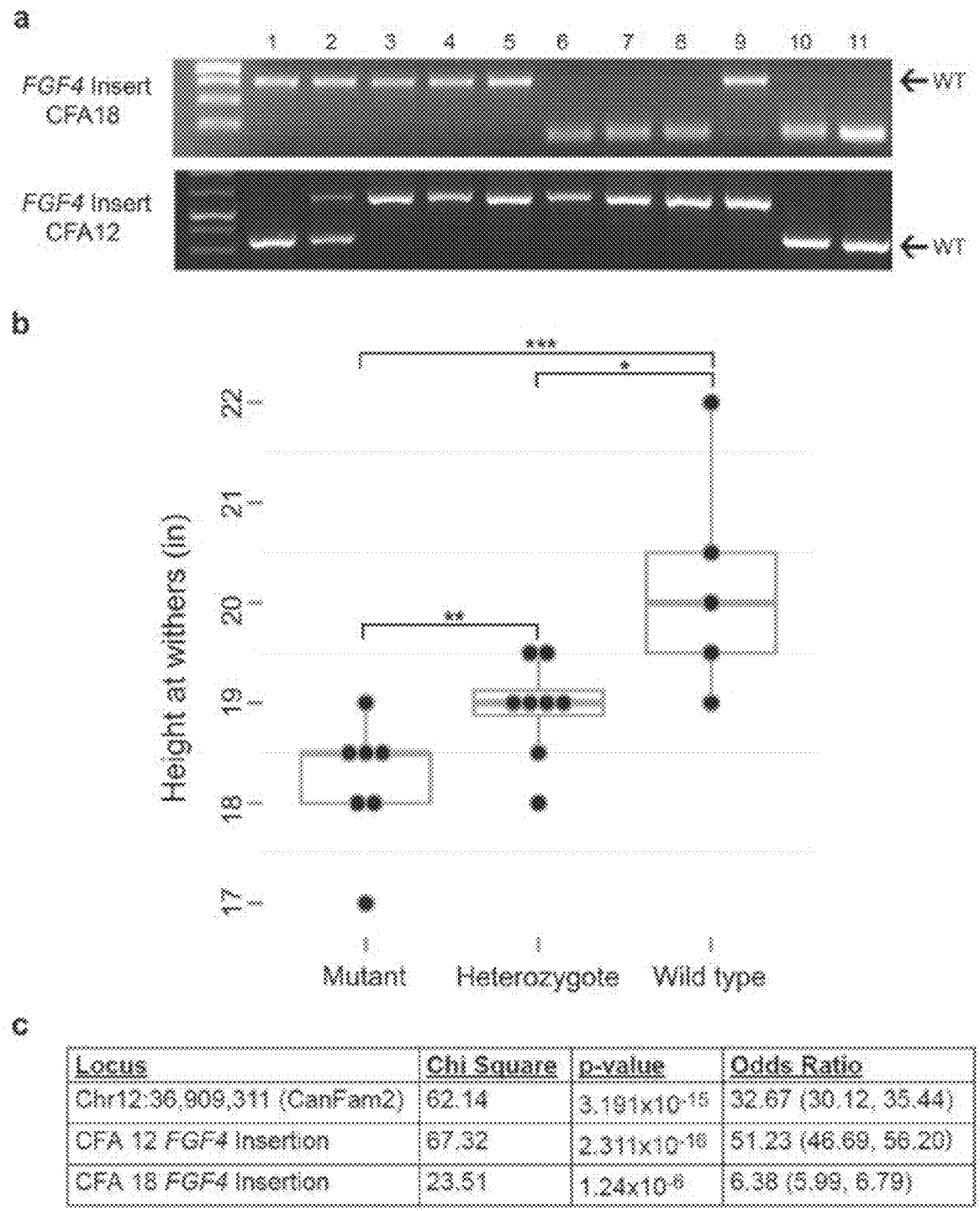
FIGS. 6A-C illustrate association of FGF4 insertion genotypes with height and IVDD: a) Genotyping results for CFA18 and CFA12 FGF4 insertions across breeds. Arrows indicate wild type (WT) band. Lane order: Ladder; 1-3) NSDTR; 4) Beagle; 5) American Cocker Spaniel; 6) Dachshund; 7) Basset Hound; 8) Pembroke Welsh Corgi; 9) Coton de Tulear; 10) Cairn Terrier; 11) West Highland White Terrier. b) Height at the withers in inches (in) was available for 7 SD NSDTR cases: all were homozygous mutant for the CFA12 FGF4 insertion, and their mean height was 18.22 in. Height was available for 13 NSDTR unaffected with SD: 5 were wild type and had a mean height of 20.2 in; 8 were heterozygous for the CFA12 FGF4 insertion and had a mean height of 18.94 in. * indicate relative levels of association of the insertion with height. *: p=0.007, : p=0.016, *: p=0.034. c) Association of various identified loci with IVDD, including Chi square, p-value, and Odds ratio (95% confidence intervals in parenthesis).

In order to assay the insertions in additional dogs, insertion and allele specific PCR based genotyping assays were developed for both the CFA12 FGF4 insertion and the previously identified CFA18 FGF4 insertion (FIG. 6a). Twelve SD NSDTR cases from the GWAS were genotyped and were homozygous for the CFA12 FGF4 insertion, while all controls were heterozygous or wild type. Additionally, IVDD cases (n=7) from the NSDTR breed were collected and were either homozygous mutant or heterozygous for the CFA12 FGF4 insertion (Table 8). All NSDTR tested for the CFA18 FGF4 insertion (n=31) were wild type, including SD and IVDD cases. NSDTRs with known height (n=20 males) at the withers were also genotyped for the CFA12 FGF4 insertion to investigate the association of height with genotype status. Height and genotype were significantly associated in a dose dependent manner when comparing wild type, heterozygous, and homozygous dogs (FIG. 6b).

TABLE 8

CFA12 FGF4 insert genotyping results for an additional 40 IVDD cases

| Breed | Wild type | Heterozygous | Mutant |
|---|---|---|---|
| Bichon Frise | 0 | 1 | 2 |
| Chihuahua | 0 | 2 | 0 |
| Dachshund | 0 | 0 | 17 |
| Dandie Dinmont Terrier | 0 | 1 | 0 |
| Mix | 0 | 6 | 4 |
| Nova Scotia Duck Tolling Retriever | 0 | 5 | 2 |

To assess the significance of association of the CFA12 FGF4 insertion with IVDD across breeds, dogs used in the IVDD GWAS were genotyped for both insertions. All dogs' genotypes were concordant with phenotype except for one case, a Rottweiler (Table 9). When associated with IVDD, the CFA12 FGF4 insertion was more highly associated than both the most highly associated SNP from the GWAS, as well as the CFA18 FGF4 insertion (FIG. 6c). To further investigate the association of the CFA12 FGF4 insertion with IVDD, 33 additional cases were genotyped for the CFA12 FGF4 insertion: 10 were heterozygous and 23 were homozygous for the CFA 12 FGF4 insertion (Table 8).

TABLE 9

CFA18 and CFA12 FGF4 insert genotype for 34 IVDD cases
and 31 controls used in the across breed IVDD GWAS

| Breed of Dog Genotyped | Case or Control | CFA18 FGF4 Insert Genotype | | | CFA12 FGF4 Insert Genotype | | |
|---|---|---|---|---|---|---|---|
| | | WT | Heterozygous | Mutant | WT | Heterozygous | Mutant |
| Basset Hound | Case (n = 1) | 0 | 0 | 1 | 0 | 0 | 1 |
| Beagle | Case (n = 1) | 1 | 0 | 0 | 0 | 0 | 1 |
| Cardigan Welsh Corgi | Case (n = 1) | 0 | 1 | 0 | 0 | 1 | 0 |
| Chihuahua | Case (n = 3) | 1 | 2 | 0 | 0 | 3 | 0 |
| Coton de Tulear | Case (n = 6) | 0 | 2 | 4 | 0 | 1 | 5 |
| Dachshund | Case (n = 3) | 0 | 0 | 3 | 0 | 0 | 3 |
| French Bulldog | Case (n = 3) | 3 | 0 | 0 | 0 | 0 | 3 |
| Maltese | Case (n = 1) | 0 | 0 | 1 | 0 | 0 | 1 |
| Mix | Case (n = 10) | 1 | 4 | 5 | 0 | 6 | 4 |
| NSDTR | Case (n = 1) | 1 | 0 | 0 | 0 | 1 | 0 |
| Pembroke Welsh Corgi | Case (n = 1) | 0 | 0 | 1 | 0 | 0 | 1 |
| Miniature Poodle | Case (n = 1) | 0 | 1 | 0 | 0 | 0 | 1 |
| Rottweiler | Case (n = 1) | 1 | 0 | 0 | 1 | 0 | 0 |
| Shih Tzu | Case (n = 1) | 0 | 0 | 1 | 0 | 1 | 0 |
| Boston Terrier | Control (n = 3) | 3 | 0 | 0 | 3 | 0 | 0 |
| Brittany | Control (n = 3) | 3 | 0 | 0 | 3 | 0 | 0 |
| Bulldog | Control (n = 1) | 1 | 0 | 0 | 1 | 0 | 0 |
| Collie | Control (n = 2) | 2 | 0 | 0 | 2 | 0 | 0 |
| Coton de Tulear | Control (n = 6) | 0 | 0 | 6 | 2 | 4 | 0 |
| Dalmatian | Control (n = 1) | 1 | 0 | 0 | 1 | 0 | 0 |
| Ibizan Hound | Control (n = 2) | 2 | 0 | 0 | 2 | 0 | 0 |
| Jack Russel Terrier | Control (n = 1) | 1 | 0 | 0 | 1 | 0 | 0 |
| Lacy Dog | Control (n = 1) | 1 | 0 | 0 | 1 | 0 | 0 |
| Poodle | Control (n = 1) | 1 | 0 | 0 | 1 | 0 | 0 |
| Shetland Sheepdog | Control (n = 2) | 2 | 0 | 0 | 2 | 0 | 0 |
| Whippet | Control (n = 3) | 3 | 0 | 0 | 3 | 0 | 0 |
| Mix | Control (n = 4) | 4 | 0 | 0 | 4 | 0 | 0 |
| Yorkshire Terrier | Control (n = 1) | 0 | 1 | 0 | 1 | 0 | 0 |

Figure 7:
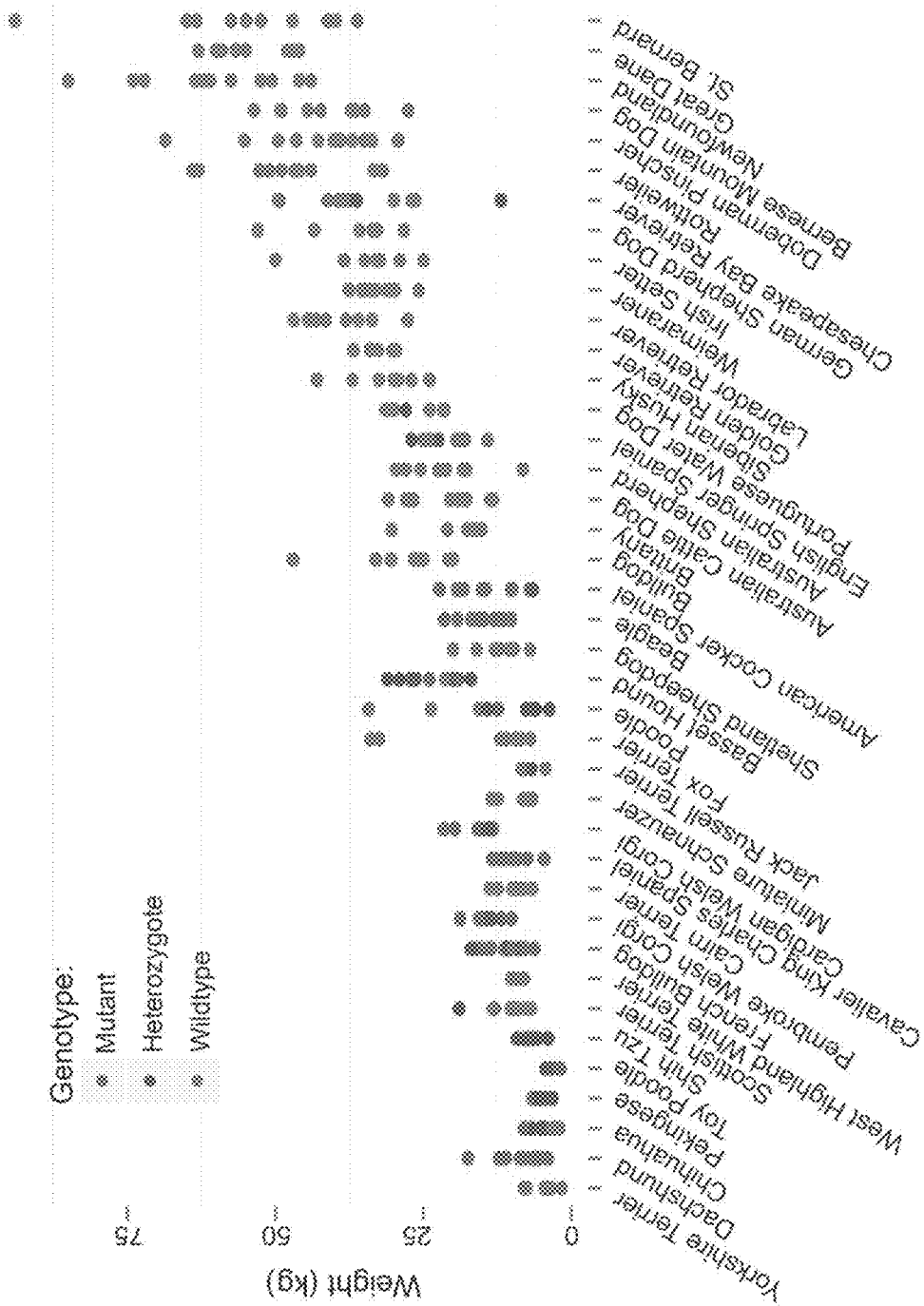
FIG. 7 illustrates CFA 12 FGF4 Genotypes Across Breeds: Genotypes for the CFA12 FGF4 insertion across dog breeds ordered by breed standard height from shortest to tallest (x-axis), plotted by dog weight in kilograms (kg)

In order to investigate the breed distribution of the retrogene insertion, 568 dogs from 50 breeds were genotyped (Table 10). The CFA12 FGF4 insertion segregates in the majority of breeds where it occurs and is present in small and medium sized dog breeds with high frequency (FIG. 7). Interestingly, all of the dogs with the CFA12 FGF4 insertion also have large external ears (pinnae), which is consistent with the phenotype seen in the NSDTR.

TABLE 10

Genotyping results for 568 dogs from 50
different breeds for CFA12 FGF4 insertion.
Breeds listed in bold showed segregation

| Breed | Wild type | Heterozygous | Mutant |
|---|---|---|---|
| American Cocker Spaniel | 0 | 1 | 9 |
| Australian Cattle Dog | 10 | 0 | 0 |
| Australian Shepherd | 10 | 0 | 0 |
| Basset Hound | 1 | 5 | 5 |
| Beagle | 0 | 1 | 17 |
| Bernese Mountain Dog | 10 | 0 | 0 |
| Boston Terrier | 3 | 0 | 0 |
| Brittany | 14 | 0 | 0 |
| Bulldog | 11 | 0 | 0 |
| Cairn Terrier | 9 | 0 | 0 |
| Cane Corso | 5 | 0 | 0 |
| Cardigan Welsh Corgi | 1 | 2 | 5 |
| Cavalier King Charles Spaniel | 0 | 0 | 9 |
| Chesapeake Bay Retriever | 29 | 7 | 0 |
| Chihuahua | 5 | 6 | 2 |
| Collie | 2 | 0 | 0 |
| Coton de Tulear | 2 | 5 | 5 |
| Dachshund | 0 | 1 | 27 |
| Dalmatian | 1 | 0 | 0 |
| Doberman Pinscher | 15 | 0 | 0 |
| English Springer Spaniel | 7 | 2 | 0 |
| Fox Terrier | 10 | 0 | 0 |
| French Bulldog | 0 | 4 | 28 |
| German Shepherd Dog | 10 | 0 | 0 |
| Golden Retriever | 10 | 0 | 0 |
| Great Dane | 10 | 0 | 0 |
| Ibizan Hound | 3 | 0 | 0 |
| Irish Setter | 8 | 0 | 0 |
| Jack Russell Terrier | 1 | 1 | 9 |
| Labrador Retriever | 10 | 0 | 0 |
| Lacy Dog | 1 | 0 | 0 |
| Maltese | 0 | 0 | 1 |
| Miniature Schnauzer | 9 | 1 | 0 |
| Mix | 4 | 6 | 4 |
| Newfoundland | 14 | 0 | 0 |
| Nova Scotia Duck Tolling Retriever | 6 | 15 | 12 |
| Pekingese | 2 | 5 | 1 |
| Pembroke Welsh Corgi | 0 | 2 | 7 |
| Poodle | 4 | 7 | 4 |
| Portuguese Water Dog | 8 | 1 | 0 |
| Rottweiler | 11 | 0 | 0 |
| Scottish Terrier | 9 | 1 | 0 |
| Shetland Sheepdog | 12 | 0 | 0 |
| Shih Tzu | 3 | 8 | 1 |
| Siberian Husky | 10 | 0 | 0 |
| Saint Bernard | 10 | 0 | 0 |
| Weimaraner | 10 | 0 | 0 |
| West Highland White Terrier | 10 | 0 | 0 |

TABLE 10-continued

Genotyping results for 568 dogs from 50
different breeds for CFA12 FGF4 insertion.
Breeds listed in bold showed segregation

| Breed | Wild type | Heterozygous | Mutant |
|---|---|---|---|
| Whippet | 3 | 0 | 0 |
| Yorkshire Terrier | 11 | 0 | 0 |

Based on occurrence of IVDD at the Pritchard Veterinary Medicine Teaching Hospital at UC Davis, the breeds with a statistically higher frequency of IVDD are also those with a higher frequency of the CFA12 FGF4 insert allele, while the breeds with a statistically lower frequency of IVDD are those with a lower frequency of the CFA12 FGF4 insert allele (Table 6).

To investigate the gene expression environment in which FGF4 inserted on CFA12, semi-quantitative RT-PCR was performed for genes across the IVDD associated interval. Using cDNA derived from neonatal vertebral body (VB) and IVD, skeletal muscle, and testis, expression levels of genes across the CFA12 associated interval were assayed in a Beagle case and Cane Corso or Labrador Retriever control, including: COL9A1, SMAP1, B3GAT2, OGFRL1, LINC00472, RIMS1, KCNQ5, and COL12A1. Expression differences between case and control were not apparent in these genes; however, we confirmed that all except RIMS1 are expressed in both neonatal VB and IVD, supporting that FGF4 inserted itself in a gene milieu conducive to expression in IVD. Semi-q PCR for total FGF4 (endogenous and retrogene products) in the same tissues showed increased expression across all tested tissue types in the case versus the control (FIG. 8).

In order to evaluate the effect of the CFA12 FGF4 retrogene insertion on overall FGF4 transcript levels, quantitative RT-PCR was performed. A comparison between samples homozygous for the CFA12 FGF4 insertion and samples with only the endogenous copy of FGF4 (i.e. wild type for both the CFA12 and CFA18 FGF4 insertions) showed a 19.47× higher (p=0.02857) and 2.16× higher (p=0.02857) expression of FGF4 in neonatal IVD and VB, respectively (FIG. 9).

Discussion

In this study, we report the identification of a FGF4 retrogene insertion in the dog genome responsible for chondrodystrophy across dog breeds, characterized by both short limbs and susceptibility to Hansen's type I intervertebral disc disease. A region was identified on CFA12 due to association with a segregating form of skeletal dysplasia observed in the NSDTR. While NSDTRs can be variably affected, the use of severely affected dogs enabled identification of the locus through GWAS. Haplotype sharing with chondrodystrophoid breeds and genome-wide association analysis for type I IVDD identified the same region on CFA12. Evaluation of mismapped mate pairs allowed the identification of a novel FGF4 retrogene, which leads to an about 20 fold increase in expression of FGF4 in neonatal intervertebral disc. Due to the embryonic expression pattern of FGF4, it is probable that these expression changes are also impacting endochondral ossification. This is the second FGF4 retrogene identified in dogs that affects limb length. While the FGF4 retrogene on CFA18 impacts limb length, the FGF4 retrogene on CFA12 explains the chondrodystrophoid phenotype, which includes limb length and IVDD (significant odds ratio>50).

Fibroblast Growth Factor 4 (FGF4) is a growth factor gene expressed in specific tissues and at specific times throughout embryonic development in the mouse (39). FGF4 is highly expressed in the apical ectodermal ridge of the developing limb bud, as well as somites and the notochord that will form the vertebral column and IVDs (39-41). FGF signaling is required for appropriate embryonic axial growth and segmentation, and FGF4/FGF8 murine hypomorphs are characterized by altered vertebral morphology and smaller limb buds (42, 43). Additionally, FGF8 hypomorphs are observed to have either hypoplastic or nonexistent external ear structures (44). In mice, creation of a gain of function FGF4 copy to replace an inactive FGF8 gene was able rescue limb development; however, it also caused abnormal tissue deposition and postaxial polydactyly, highlighting that levels of FGF throughout embryonic development must be properly controlled for normal limb formation (32). While the specific embryonic expression pattern of FGF4 in dogs with 4-6 copies of the gene is unknown, we hypothesize that the insertion site milieu on CFA12 versus CFA18 is contributing to differences in expression between the retrogenes, leading to the differences in phenotype.

A survey of retrogenes in the canine reference genome reported about 70 functional retrogenes in the dog; however, only the previous CFA18 FGF4 retrogene insertion has been reported to be associated with a disease causing phenotype (26, 45). Similarly in humans, the formation of processed pseudogenes in general, as well as those that retain their intended function and cause disease, is rare (46-51).

Both copies of the canine FGF4 retrogenes have signatures of having arisen from RNA retrotransposed by LINE-1 integrase and reverse transcriptase, including flanking TSDs and polyA tracts (class 1 templated sequence insertion polymorphism) (52). The CFA18 FGF4 retrogene insertion was predicted to be expressed due to insertion near sequence with promoter properties (26). While the CFA12 FGF4 insertion is placed near a potential TATA box and RNA Pol II promoter, it is more likely that the CpG island included in the retrogene is driving expression (53-55). This hypothesis is supported by the finding that a majority of retrogene expression is actually due to genomic context and contribution of CpG islands, not through the use of nearby promoters (56). To our knowledge, this is the first documentation of a second retrogene insertion of the same parental gene resulting in a disease phenotype in a mammalian species. Due to the lack of resources available to identify these types of mutations, it is likely that there are other phenotype inducing retrocopies present in the canine genome that have yet to be discovered.

Chondrodystrophy associated mutation events occurred a very long time ago, as there are descriptions of short-legged dogs dating back over 4000 years (57). In addition, both mutations occur concurrently in very unrelated dog breeds from diverse breed groupings and geographical locations. The fact that FGF4 has been retrotransposed twice in dogs in the last 3-4 thousand years makes it likely that this has happened at other times. The large CpG island in the 5' end of the endogenous FGF4 gene may enable phenotypic consequences more readily than for other retrogenes. Once the FGF4 retrogene appeared and produced an obvious phenotype, strong selection was likely applied to retain it, aided by the semi-dominant nature of the mutation.

The NSDTR is the smallest of the retriever dog breeds, and based on the association of the CFA12 FGF4 insertion with height, we hypothesize that the heterozygous phenotype is aesthetically desirable and that selection is maintaining the insertion at a relatively high allele frequency. Investigation of the CFA12 FGF4 insertion in additional breeds also showed high allele frequency in multiple small and medium sized dog breeds. In breeds also containing the CFA18 FGF4 insertion, there is an even more dramatic decrease in height (e.g. Basset Hound, Cardigan Welsh Corgi, Dachshund, etc.), supporting that both FGF4 retrogenes affect long bone length.

In addition to segregating with height, the CFA12 FGF4 insertion also segregates with Hansen's type I IVDD susceptibility. Of the IVDD cases genotyped for the CFA12 FGF4 insertion, all were homozygous mutant or heterozygous, except for 1, suggesting that one additional copy of FGF4 on CFA12 is sufficient to cause type I IVDD. The single discordant case was a Rottweiler, a breed that does not fit the chondrodystrophic phenotype. It is possible that there is another cause of IVDD in nonchondrodystrophoid dog breeds occurring without endochondral ossification defects (9). IVDD-affected NSDTRs were also all either homozygous or heterozygous for the CFA12 FGF4 insertion. Given that the CFA18 FGF4 insertion is not found in the NSDTR and was inconsistently present in the IVDD cases tested, this further supports that the identified insertion on CFA12 is causing both short limbs and Hansen's type I IVDD in both the NSDTR and across dog breeds.

The breeds with a higher frequency of the CFA12 FGF4 insertion are the same breeds identified in the last 50 years as being predisposed to IVDD. Presence of the CFA18 FGF4 insertion is common in many breeds with IVDD, and it is possible that it may contribute to the disease; however, previous mapping within Dachshunds, which are reported "fixed" for the CFA18 FGF4 insertion, actually show segregation of the associated haplotype on chromosome 12 with IVDD, supporting that the CFA12 FGF4 insertion is the critical factor determining disease status (26, 35). Of particular interest is the lack of reports of IVDD cases in breeds such as the Cairn Terrier and West Highland White Terrier, both of which have the CFA18 FGF4 insertion, but not the CFA12 FGF4 insertion. Similarly, the high incidence of IVDD in breeds such as the American Cocker Spaniel, Beagle, and French Bulldog that do not have the CFA18 FGF4 insertion but a high frequency of the CFA12 FGF4 insertion supports that FGF4 specifically from CFA12 is contributing to the IVDD phenotype.

The segregation of the CFA12 FGF4 insertion within dog breeds presents an opportunity for improvement of animal health, as implementation of genetic testing over time could lead to the elimination of type I IVDD. Based on the ever-growing popularity of some breeds, the number of animals with this intervertebral disc disease mutation across the globe is in the millions. Myelopathy secondary to IVD herniation is the most commonly presenting neurological disorder of the spinal cord in dogs (58). The overall heath and financial consequences across the spectrum of presentations in companion dogs is immense. Prevention of disease through breeding and eradication has the potential for far-reaching benefits beyond those achievable through advances in surgical or medical therapy.

Additionally, the dog may serve as a valuable human-animal model for IVDD. Administration of a tyrosine kinase inhibitor in a mouse model with a gain of function mutation in FGFR3 has been shown to overcome growth defects associated with altered FGF signaling (33). Based on the phenotype and molecular etiology of chondrodystrophy and IVDD in dogs, it has the potential to serve as a bridge between mouse and human studies evaluating the efficacy of targeted pharmacological treatment of FGF based genetic disorders.

Given the high mortality rate of IVDD and the high cost of surgery, identification of this susceptibility locus could provide a valuable tool for owners, breeders, and veterinarians for mitigating risk of intervertebral disc herniation and resulting myelopathy (9). This could be especially useful in breeds that have both the CFA12 and CFA18 FGF4 retrogene, as they could breed away from the CFA12 FGF4 retrogene, while still maintaining the aesthetically desirable shortness in stature contributed by the CFA18 FGF4 retrogene. In breeds with only the CFA12 FGF4 retrogene, breeders will ultimately decide if prevention of Hansen's type I IVDD outweighs any potential loss of shortness (or gain in height).

REFERENCES

1. Hansen, H.-J. A pathologic-anatomical study on disc degeneration in dog: with special reference to the so-called enchondrosis intervertebralis. Acta Orthop Scand 23, 1-130 (1952).
2. Hansen, H.-J. A pathologic-anatomical interpretation of disc degeneration in dogs. Acta Orthop Scand 20, 280-293 (1951).
3. Braund, K., Ghosh, P., Taylor, T. & Larsen, L. Morphological studies of the canine intervertebral disc. The assignment of the beagle to the achondroplastic classification. Res Vet Sc 19, 167-172 (1975).
4. Martinez, S., Fajardo, R., Valdés, J., Ulloa-Arvizu, R. & Alonso, R. Histopathologic study of long-bone growth plates confirms the basset hound as an osteochondrodysplastic breed. Can J Vet Res 71, 66 (2007).
5. Bray, J. P. & Burbidge, H. The canine intervertebral disk. Part Two: Degenerative changes-nonchondrodystrophoid versus chondrodystrophoid disks. J Am Anim Hosp Assoc 34, 135-144 (1998).
6. Hunter, C. J., Matyas, J. R. & Duncan, N. A. The three-dimensional architecture of the notochordal nucleus pulposus: novel observations on cell structures in the canine intervertebral disc. J Anat 202, 279-291 (2003).
7. Cappello, R., Bird, J. L., Pfeiffer, D., Bayliss, M. T. & Dudhia, J. Notochordal cell produce and assemble extracellular matrix in a distinct manner, which may be responsible for the maintenance of healthy nucleus pulposus. Spine 31, 873-882 (2006).
8. Kranenburg, H.-J. C. et al. Intervertebral disc disease in dogs Part 2: Comparison of clinical, magnetic resonance imaging, and histological findings in 74 surgically treated dogs. Vet J 195, 164-171 (2013).
9. Bergknut, N. et al. Incidence of intervertebral disk degeneration-related diseases and associated mortality rates in dogs. J Am Vet Med Assoc 240, 1300-1309 (2012).
10. Bergknut, N. et al. The dog as an animal model for intervertebral disc degeneration? Spine 37, 351-358 (2012).
11. Sakai, D., Nakai, T., Mochida, J., Alini, M. & Grad, S. Differential phenotype of intervertebral disc cells: microarray and immunohistochemical analysis of canine nucleus pulposus and anulus fibrosus. Spine 34, 1448-1456 (2009).
12. Oegema, T. The role of disc cell heterogeneity in determining disc biochemistry: a speculation. Biochem Soc Trans 30, 839-844 (2002).

13. Priester, W. A. Canine intervertebral disc disease Occurrence by age, breed, and sex among 8,117 cases. Theriogenology 6, 293-303 (1976).
14. Fluehmann, G., Doherr, M. & Jaggy, A. Canine neurological diseases in a referral hospital population between 1989 and 2000 in Switzerland. J Small Anim Pract 47, 582-587 (2006).
15. Brisson, B. A., Moffatt, S. L., Swayne, S. L. & Parent, J. M. Recurrence of thoracolumbar intervertebral disk extrusion in chondrodystrophic dogs after surgical decompression with or without prophylactic fenestration: 265 cases (1995-1999). J Am Vet Med Assoc 224, 1808-1814 (2004).
16. Ball, M., McGuire, J., Swaim, S. & Hoerlein, B. Patterns of occurrence of disk disease among registered dachshunds. J Am Vet Med Assoc 180, 519-522 (1982).
17. Bellumori, T. P., Famula, T. R., Bannasch, D. L., Belanger, J. M. & Oberbauer, A. M. Prevalence of inherited disorders among mixed-breed and purebred dogs: 27,254 cases (1995-2010). J Am Vet Med Assoc 242, 1549-1555 (2013).
18. Lappalainen, A. K., Vaittinen, E., Junnila, J. & Laitinen-Vapaavuori, O. Intervertebral disc disease in Dachshunds radiographically screened for intervertebral disc calcifications. Acta Vet Scand 56, 89 (2014).
19. Bergknut, N. et al. Incidence And Mortality Of Diseases Related To Intervertebral Disc Degeneration In A Population Of Over 600,000 Dogs. J Vet Intern Med 26, 847 (2012).
20. NOMENCLATURE FOR CONSTITUTIONAL (INTRINSIC) DISEASES OF BONES. Pediatrics 47, 431-434 (1971).
21. Warman, M. L. et al. Nosology and classification of genetic skeletal disorders: 2010 revision. Am J Med Genet A 155A (2011).
22. Frischknecht, M. et al. A COL11A2 Mutation in Labrador Retrievers with Mild Disproportionate Dwarfism. 8, e60149 (2013).
23. Goldstein, O. et al. COL9A2 and COL9A3 mutations in canine autosomal recessive oculoskeletal dysplasia. Mamm Genome 21, 398-408 (2010).
24. Neff, M. W. et al. Partial deletion of the sulfate transporter SLC13A1 is associated with an osteochondrodysplasia in the Miniature Poodle breed. PloS one 7, e51917 (2012).
25. Kyöstilä, K., Lappalainen, A. K. & Lohi, H. Canine chondrodysplasia caused by a truncating mutation in collagen-binding integrin alpha subunit 10. PloS one 8, e75621 (2013).
26. Parker, H. G. et al. An expressed fgf4 retrogene is associated with breed-defining chondrodysplasia in domestic dogs. Science 325, 995-998 (2009).
27. Shiang, R. et al. Mutations in the transmembrane domain of FGFR3 cause the most common genetic form of dwarfism, achondroplasia. Cell 78, 335-342 (1994).
28. Langer J R, L. O., Baumann, P. A. & Gorlin, R. J. Achondroplasia: clinical radiologic features with comment on genetic implications. Clin Pediatr (Phila) 7, 474-485 (1968).
29. Rousseau, F. et al. Mutations in the gene encoding fibroblast growth factor receptor-3 in achondroplasia. Nature 371, 252 (1994).
30. Naski, M. C., Wang, Q., Xu, J. & Ornitz, D. M. Graded activation of fibroblast growth factor receptor 3 by mutations causing achondroplasia and thanatophoric dysplasia. Nat Genet 13, 233-237 (1996).
31. Gibson, B. G. & Briggs, M. D. The aggrecanopathies; an evolving phenotypic spectrum of human genetic skeletal diseases. Orphanet J Rare Dis 11, 86 (2016).
32. Lu, P., Minowada, G. & Martin, G. R. Increasing Fgf4 expression in the mouse limb bud causes polysyndactyly and rescues the skeletal defects that result from loss of Fgf8 function. Development 133, 33-42 (2006).
33. Komla-Ebri, D. et al. Tyrosine kinase inhibitor NVP-BGJ398 functionally improves FGFR3-related dwarfism in mouse model. J Clin Invest 126, 1871 (2016).
34. Dailey, L., Ambrosetti, D., Mansukhani, A. & Basilico, C. Mechanisms underlying differential responses to FGF signaling. Cytokine Growth Factor Rev 16, 233-247 (2005).
35. Mogensen, M. S. et al. Genome-Wide Association Study in Dachshund: Identification of a Major Locus Affecting Intervertebral Disc Calcification. The Journal of heredity 102, S81-S86 (2011).
36. Quignon, P. et al. Fine Mapping a Locus Controlling Leg Morphology in the Domestic Dog. Cold Spring Harb Symp Quant Biol (2009).
37. Kierczak, M. et al. cgmisc: Enhanced Genome-wide Association Analyses and Visualisation. Bioinformatics, btv426 (2015).
38. Solovyev, V. V., Shahmuradov, I. A. & Salamov, A. A. Identification of promoter regions and regulatory sites. Methods in molecular biology (Clifton, N.J.) 674, 57-83 (2010).
39. Niswander, L. & Martin, G. R. Fgf-4 expression during gastrulation, myogenesis, limb and tooth development in the mouse. Development 114, 755-768 (1992).
40. Bagnall, K., Higgins, S. & Sanders, E. The contribution made by a single somite to the vertebral column: experimental evidence in support of resegmentation using the chick-quail chimaera model. Development 103, 69-85 (1988).
41. Shamim, H. et al. Sequential roles for Fgf4, En1 and Fgf8 in specification and regionalisation of the midbrain. Development 126, 945-959 (1999).
42. Boulet, A. M. & Capecchi, M. R. Signaling by FGF4 and FGF8 is required for axial elongation of the mouse embryo. Dev Biol 371, 235-245 (2012).
43. Sun, X., Mariani, F. V. & Martin, G. R. Functions of FGF signalling from the apical ectodermal ridge in limb development. 418, 501-508 (2002).
44. Abu-Issa, R., Smyth, G., Smoak, I., Yamamura, K.-i. & Meyers, E. N. Fgf8 is required for pharyngeal arch and cardiovascular development in the mouse. Development 129, 4613-4625 (2002).
45. Pan, D. & Zhang, L. Burst of young retrogenes and independent retrogene formation in mammals. PloS one 4, e5040 (2009).
46. Kubiak, M. R. & Makalowska, I. Protein-Coding Genes' Retrocopies and Their Functions. Viruses 9, 80 (2017).
47. Hancks, D. C. & Kazazian, H. H. Active human retrotransposons: variation and disease. 22(2012).
48. de Boer, M. et al. Primary Immunodeficiency Caused by an Exonized Retroposed Gene Copy Inserted in the CYBB Gene. Hum Mutat 35, 486-496 (2014).
49. Breyer, J. P. et al. An expressed retrogene of the master embryonic stem cell gene POU5F1 is associated with prostate cancer susceptibility. Am J Hum Genet 94, 395-404 (2014).
50. Demars, J. et al. Genome-wide Identification Of The Mutation Underlying Fleece Variation And Discriminating Ancestral Hairy Species From Modern Woolly Sheep. Mol Biol Evol (2017).

51. Geister, K. A. et al. LINE-1 Mediated Insertion into Poc1a (Protein of Centriole 1 A) Causes Growth Insufficiency and Male Infertility in Mice. PLoS Genet 11, e1005569 (2015).
52. Onozawa, M., Goldberg, L. & Aplan, P. D. Landscape of insertion polymorphisms in the human genome. Genome Biol Evol 7, 960-968 (2015).
53. Antequera, F. Structure, function and evolution of CpG island promoters. Cell Mol Life Sci 60, 1647-1658 (2003).
54. Hannenhalli, S. & Levy, S. Promoter prediction in the human genome. Bioinformatics 17, S90-S96 (2001).
55. Ioshikhes, I. P. & Zhang, M. Q. Large-scale human promoter mapping using CpG islands. Nat Genet 26, 61-63 (2000).
56. Carelli, F. N. et al. The life history of retrocopies illuminates the evolution of new mammalian genes. Genome Res 26, 301-314 (2016).
57. Morris, D. Dogs: a dictionary of dog breeds, (Trafalgar Square Pub., 2002).
58. Packer, R. M. A., Hendricks, A., Volk, H. A., Shihab, N. K. & Burn, C. C. How Long and Low Can You Go? Effect of Conformation on the Risk of Thoracolumbar Intervertebral Disc Extrusion in Domestic Dogs. PloS one 8, e69650 (2013).
59. Purcell, s. et al. PLINK, a tool set for whole-genome association and population-based linkage analyses. 81 (2007).
60. Bolger, A. M., Lohse, M. & Usadel, B. Trimmomatic: a flexible trimmer for Illumina sequence data. Bioinformatics 30, 2114-20 (2014).
61. Hoeppner, M. P. et al. An improved canine genome and a comprehensive catalogue of coding genes and non-coding transcripts. PloS one 9, e91172 (2014).
62. Li, H. & Durbin, R. Fast and accurate short read alignment with Burrows-Wheeler transform. Bioinformatics 25, 1754-60 (2009).
63. Picard Tools.
64. McKenna, A. et al. The Genome Analysis Toolkit: a MapReduce framework for analyzing next-generation DNA sequencing data. Genome Res 20, 1297-303 (2010).
65. Rozen, S. & Skaletsky, H. Primer3 on the WWW for general users and for biologist programmers. Methods in molecular biology (Clifton, N.J.) 132, 365-86 (2000).
66. Brinkhof, B., Spee, B., Rothuizen, J. & Penning, L. C. Development and evaluation of canine reference genes for accurate quantification of gene expression. Anal Biochem 356, 36-43 (2006).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

Sequence ID No: 1 - 5' Breakpoint of FGF4 insertion on CFA12 at 33,710,178. Bolded and underlined text at nucleotide residues 1002-2001 shows insertion sequence.
TTCCTCAGACTCAGTTTCCCATTTGAAAGCAAGAAACTTTAGTTGGGCACTAGCCATTTCA
GTTGGATTCCTTACTATGTCTTACTTCTCCCAAGAAGTTATTCCTTCCTATCTATCCATTG
TATTAAGAAAGGCAGATTAGTTTTCCCATAGCCATCTGTTTATTTGGCCTATTGTCTTATG
ATTTCTCAAAACCAACACAGGTATTCCCAGGGTCATCTGTGACATCTGCCAAGCTGCCTGG
GGAGCAGAGTCATATCTAGACATAACATGTGAAGGAGGTCATGTTTTGGTTGGCGGGGAGC
TTTTTGGTTCTTTTTCTACCCAGAAGTCTCTTTTGTCTCCTTAGATGTCTCTTCTGTATTT
ATAGCTAGTCTTGGAGCATTGCTTTTTCCTACCTGTAAACTAAAGCGACAGTTCATAAAAC
TTCATATGTCTTTTTTTCTCTTACTCATTTTGTTTTGTTTTACTTTTCCCAATTATAAATT
ACATGACATTTAGAGAAAATTTGGAAAATATAAAGTTAAAAAGTTATAGACAGTACAACTC
CCACACATAATCATGGCTAACATGGTGTATTTTTTATTCCTTCTTGGCTTGTATTTAGGTG
TAATTTAAGAAAACTCTTCAAAATCCAAAGGGATAAGTTTAAGCAATTAAACAAATGGAAC
TGGTGAATAACAGCTGGCATGGTCAGTTATTTCTGTCTGAGGATCAGGGAGGGTTTGATGG
AAGAGTTAATATTTCTGTTAGGTTTGAGAGTATAAATAGAATTTTGAAGAAGAGTGAATAA
GGAAAAAAAATCCTATGATAAAAGAAAAACGTGGAAGCATTAAAGTATACATATATATGAA
TAATTAATGGCTGACTGTGGTCCTGAAGACTCTATTAAAATTTTGTGCTTTAGTTTCCTTG
TTTATGCATTGGGGAGAGTCATATTTGTCTTTTTATCTTTCTAGAAAATGGAATATGTTAA
GATAATTCCTATTCAAGTGCTTTGAGGCGGAGGGAGGCGCGCACCGCTCCGGAGGGTCCCA
GCCCGGCCGCGCGTCCCGCCCGCCGCCCGCCGCCCGCCGCTCCATGCAGCCCGGGTAGCCC
CGGCGCCCGGGGGCCCCGCGCCTCGCCTCCCGCTCCGCCTGCGGCCGCGCGCTCCGCACCG
AGTCCCGGCCGTGCGCTCCCGCGGGCCGCCACAGGCGCAGCTCGGCCCCGCGGCTTCCCGG
GCGCACGGCCCGAGGGCGGGGATGGCGGGGCCCGGGGCGGCCGCGGCGGCGCTGCTCCCGG
CGGTCCTGCTGGCGGTGCTGGCGCCCTGGGCCGGCCGCGGGGGCGCCGCCGCTCCCACCGC
CCCCAACGGCACGCTGGGCGCCGAGCTGGAGCGCCGCTGGGAGAGCCTGGTGGTGCGCTCG
CTGGCGCGCCTGCCGGTGGCCGCGCAGCCCAAGGAGGCGGCCGTCCAGAGCGGCGCCGGCG
ACTACCTCCTGGGCATCAAGCGGCTGCGGCGGCTCTACTGCAACGTGGGCATCGGCTTCCA
CCTCCAGGTGCTCCCCGACGGCCGCATCGGCGGCGTGCACGCGGACACGAGCGACAGCCTG
CTGGAGCTCTCGCCGGTGGAGCGGGGCGTGGTGAGCATCTTCGGCGTGGCCAGCCGGTTCT
TCGTGGCCATGAGCAGCAAGGGCAAGCTGTACGGCTCGCCCTTCTTCACCGAGGAGTGCAA
GTTCAAAGAGATCCTGCTCCCCAACAACTACAATGCCTACGAGTGCTGCAGGTACCCGGGC
ATGTTCATTGCCCTGAGCAAGAACGGGAAGACCAAGAAAGGGAGCCGAGTGTCCCCCACCA
TGAAGGTCACCCACTTCCTCCCCAGGCTGTGACTCCAGGCATCCTGCCTCAGTTTCCCAAT
GCTCCGGAGACTTTCTCCAGATGGACAATTTAATGCCAGAGTAGGTGTAAGATATTTAAAT
TAATTATTTAAATGTGTATATATCGCCACCAAATTATTTATGGTTCTGT Sequence ID No: 2 - 3'Breakpoint of FGF4 insertion on CFA12 at 33,710,178. Bolded and underlined text at nucleotide residues 1-1000 shows insertion sequence.
AGATGGAAGAGGCAGGGTCGGTGATGTTTAAAAAAAGTCCTGAGGTGATGGCAAACATTTA
ATTTTAATGAATGACTTTTTAGAGTTTATACAAAATGACCTTAGCTCGCTACCAGAAATGC
TCCGAATGTTTTGTCAAGACTTTAATGCTCTCCTAGGATGTTTCTGAACCACCTCCCAAAT -continued

SEQUENCE LISTING

TAACTTTATGGGAGTCTACAGACAGCAAGACTGGAAAAGGCTGATTGGAGTTTGTGTCTTT
CGCATTCCTTTTTAAAACTCTTTGTTCGAATGCAAATCATCTACTTAAAATACTGTCCTTA
AACCAAGGCCTTGGAGGAGGAAGGAAGCCGCTCGTGAAGCCTGATGGCTGGACTGTACATC
TCAACCGGCCGTCCCCGTCCGTGCGGTGAAATAAAAAATGTTTTCAATTTTAAATTGCGTC
CTAGGCTCCAGGAGTCTTGAGCAGAGGGGATGCTCCCAGGTCTCGGTGCTGATGGGGGGGA
GGGGGCGGGGCTGGAATGTGTGGACATTCGGTATTTCAAATACTCGCCTCCTAAGTCTTAG
CTGCCTTGGGATGATGGCACGATGTCTCATCTCAGAGCCCAATCCGATTGTCAGGAACGAA
GATGTCTTAAGTGCAGAATGTGGTGATCCTTGGCCACTTGCTAGTCAGCGAGCCTTGTGGG
AAGCGTATAGAGATGTCATTGGACCTCTGCAATATCGCTAAGTGTTTTCTACTGTCGTGAT
GGGATCTAAGGTTTCTGTACTTTCCGCGGTTTGCAGGATCTGTCTGTAGTTTTATACAGGT
GCTGAGCCCTATTGTGATGTATGTGCTGTGCACATTGACATGCCGAATAAATGGAAACA
TTTGTCATGTATGAAAAGAACCCCATTGGACTTGATGTAAAGAACCGGGGAAGGTATTGAA
AACGATTAAAACCTGCCTGGAAATGCCATGCTAAAAAAAAAAAAAAAAAAAAAAAAAAAA
AAAAAAAAAAAAAAAGTGCTTTGAACTCTTCAAAGAAAAGACACCTCAAAATCTACAGCAT
AATTGAGGTATCAGATTTTTGCCACTTTTTACTATTATGATTTTATTCACTAGCATTTATT
TTGTCATCTAGAATTTTATTCACAAGCAAAAGCTTTTAGGAAATCATACTTATTTTAGGTT
AAATGAGAAAAAACATTAGCTTAATTTTTTCTTAGTTTTTTTAATGTTTCTGACTATGATA
TAATACCTCACAATAGCTTATAAAGTGAATTTTCAATTTCAGTCATTATTAATTTGGCTGT
CTCAAAATCAGGCTATATGTTATTCAAGTACCACTCTTTAGTGTCGTGAAAAAATCAGTA
CAGTGGGTTCAAAAACAAACATCTTAATTGCAGACACTTGCAAATAGTTCAGAGTATGTGT
TAATATGACATCTGTAACATTTCAGATATTTCTTGTTCTCAGTTTTTAAAAAAGCAATCTA
AAAAGCAACGGAACAAAGGGAAAATATTGACAAGTAATCTGCTTAAAAACCCATGTGAATA
CGTGGAAATGTCAGATCTTTACACACTGTAATCTTGAACTTCCCATGTTTTATATGCTAAA
CATTCTAGCCTCTTGTTAGTTACCAGGTCTTTTAAAATTGTATGGGATTACATTCATATTT
AAGATTGTATTCTGATTTTGCATGGACTAAATAAAAATCTACTTATTTAGACTGACAGTAA
TTTCACTGTCATTCTGCAAGTTGGGTTTTGTAGTTTTAGTAATCAAAAGTAGGTTTACTTT
TTTAAAAAACTGTAATTCAGGTGTGGTATAGAAAATAAACTCAAGTGGGTAAGAAACATCT
CAGTTCTTATTGCCTTTAAATGAAAATTAAACTAACTGATTTCAACCTCATCAGACTTCCA
GGAAACCCAATCTCAATCAGTGATGGAGTCCCTGATTCTCTTAGGATCATAGCATCTGGGA
AGTTCACATGGTATTGGATAAGGAAAAGGGCCTCTGCTGGCTAGGCCA

SEQ ID NO: 11 - oligo for detecting 5'-end of insert
TCTTTCTAGAAAATGGAATATGTTAAGATAATTCCTATTCAAGTGCTTTGAGGCGGAGGGA
GGCGCGCACCGCTCCGCAGGGTCCCAGCCCGGCCGCGCG
Wherein 5'-end of insert is at nucleic acid residue 52, and
the insertion sequence is in bold and underlined. The
oligonucleotide of SEQ ID NO: 11 is at least 20 nucleic acids
in length, comprising at least 3 nucleic acid bases flanking
either 5' or 3' of the 5'-end of insert (nucleic acid residue
number 52)

SEQ ID NO: 12 - oligo for detecting 3'-end of insert
AAAAAAGTGCTTTGAACTCTTCAAAGAAAAGACACCTCAAAATCTACAGCATAATTGAGGT
ATCA
Wherein 3'-end of insert is at nucleic acid residue 15, and
the insertion sequence is in bold and underlined. The
oligonucleotide of SEQ ID NO: 12 is at least 20 nucleic acids
in length, comprising at least 3 nucleic acid bases flanking
either 5' or 3' of the 3'-end of insert (nucleic acid residue
number 15)

What is claimed is:

1. A method comprising:
assessing a biological sample obtained from a canine for the presence of a retrogene insertion encoding canine fibroblast growth factor 4 (FGF4) inserted at a target site duplication sequence located at 33,710,168-33,710,178 on canine chromosome 12 (chr12:33,710,168-33,710,178), wherein the assessing comprises contacting genomic DNA present in the biological sample with reagents configured to detect the presence of the retrogene insertion encoding canine FGF4 located at chr12:33,710,168-33,710,178, and wherein the assessing detects the presence of the retrogene insertion encoding canine FGF4 located at chr12:33,710,168-33,710,178.

2. The method according to claim 1, wherein the sample is a blood sample.

3. The method according to claim 1, wherein the reagents comprise one or more oligonucleotide pairs configured to amplify, if present, the retrogene insertion encoding canine FGF4 inserted at the target site duplication sequence located at chr12:33,710,168-33,710,178.

4. The method according to claim 3, wherein the one or more oligonucleotide pairs are configured to detect the 5'-end of the retrogene insertion located at nucleic acid residue 1002 of SEQ ID NO:1.

5. The method according to claim 3, wherein an oligonucleotide in the one or more oligonucleotide pairs hybridizes to a sequence segment within nucleic acid residues 1-1001 of SEQ ID NO:1.

6. The method according to claim 3, wherein the one or more oligonucleotide pairs are configured to detect the 3'-end of the retrogene insertion located at nucleic acid residue 1000 of SEQ ID NO:2.

7. The method according to claim 3, wherein an oligonucleotide in the one or more oligonucleotide pairs hybridizes to a sequence segment within nucleic acid residues 1001-2000 of SEQ ID NO:2.

8. The method according to claim 1, wherein the reagents comprise polynucleotides configured to detect the presence of the retrogene insertion by hybridization.

9. The method according to claim 1, wherein the reagents are configured to detect the presence of the retrogene insertion by sequencing.

10. The method according to claim 1, wherein the canine is of a breed having a predisposition to chondrodystrophy.

11. The method according to claim 1, wherein the canine is a purebred or mix from a breed selected from the group consisting of American Cocker Spaniel, Basset Hound, Beagle, Cardigan Welsh Corgi, Chesapeake Bay Retriever, Chihuahua, Coton de Tulear, Dachshund, English Springer Spaniel, French Bulldog, Jack Russell Terrier, Miniature Schnauzer, Nova Scotia Duck Tolling Retriever, Pekingese, Pembroke Welsh Corgi, Poodle, Portuguese Water Dog, Scottish Terrier, Shih Tzu, and mixtures thereof.

12. The method according to claim 1, wherein the canine is a purebred or mix from a breed selected from the group consisting of American Cocker Spaniel, Basset Hound, Beagle, Corgi, Dachshund, French bulldog, Nova Scotia Duck Tolling Retriever, and Pekingese.

\* \* \* \* \*

SEQUENCE LISTING

<160> NUMBER OF SEQ ID NOS: 50

<210> SEQ ID NO 1
<211> LENGTH: 2001
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ttcctcagac tcagtttccc atttgaaagc aagaaacttt agttgggcac tagccatttc     60
agttggattc cttactatgt cttacttctc ccaagaagtt attccttcct atctatccat    120
tgtattaaga aaggcagatt agttttccca tagccatctg tttatttggc ctattgtctt    180
atgatttctc aaaaccaaca caggtattcc cagggtcatc tgtgacatct gccaagctgc    240

```
ctggggagca gagtcatatc tagacataac atgtgaagga ggtcatgttt tggttggcgg      300 ggagctttt  ggttcttttt ctacccagaa gtctcttttg tctccttaga tgtctcttct      360
gtatttatag ctagtcttgg agcattgctt tttcctacct gtaaactaaa gcgacagttc      420
ataaaacttc atatgtcttt ttttctctta ctcattttgt tttgttttac ttttcccaat      480
tataaattac atgacattta gagaaaattt ggaaaatata aagttaaaaa gttatagaca      540
gtacaactcc cacacataat catggctaac atggtgtatt ttttattcct tcttggcttg      600
tatttaggtg taatttaaga aaactcttca aaatccaaag ggataagttt aagcaattaa      660
acaaatggaa ctggtgaata acagctggca tggtcagtta tttctgtctg aggatcaggg      720
agggtttgat ggaagagtta atatttctgt taggtttgag agtataaata gaattttgaa      780
gaagagtgaa taaggaaaaa aaatcctatg ataaaagaaa aacgtggaag cattaaagta      840
tacatatata tgaataatta atggctgact gtggtcctga agactctatt aaaattttgt      900
gctttagttt ccttgtttat gcattgggga gagtcatatt tgtctttta  tctttctaga      960 aaatggaata tgttaagata attcctattc aagtgctttg aggcgcaggg aggcgcgcac     1020
cgctccgcag ggtcccagcc cggccgcgcg tcccgcccgc cgcccgccgc ccgccgctcc     1080
atgcagcccg ggtagcccg  gcgcccgggg gccccgcgcc tcgcctcccg ctccgcctgc     1140
ggccgcgcgc tccgcaccga gtcccggccg tgcgctcccg cgggccgcca caggcgcagc     1200
tcggccccgc ggcttcccgg gcgcacggcc cgagggcggg gatggcgggg cccggggcgg     1260
ccgcggcggc gctgctcccg gcggtcctgc tggcggtgct ggcgccctgg gccggccgcg     1320
ggggcgccgc cgctcccacc gccccccaacg gcacgctggg cgccgagctg gagcgccgct     1380
gggagagcct ggtggtgcgc tcgctggcgc gcctgccggt ggccgcgcag cccaaggagg     1440
cggccgtcca gagcggcgcc ggcgactacc tcctgggcat caagcggctg cggcggctct     1500
actgcaacgt gggcatcggc ttccacctcc aggtgctccc cgacggccgc atcggcggcg     1560
tgcacgcgga cacgagcgac agcctgctgg agctctcgcc ggtggagcgg ggcgtggtga     1620
gcatcttcgg cgtggccagc cggttcttcg tggccatgag cagcaagggc aagctgtacg     1680
gctcgccctt cttcaccgag gagtgcaagt tcaaagagat cctgctcccc aacaactaca     1740
atgcctacga gtgctgcagg tacccgggca tgttcattgc cctgagcaag aacgggaaga     1800
ccaagaaagg gagccgagtg tccccccacca tgaaggtcac ccactcctc cccaggctgt     1860 gactccaggc atcctgcctc agtttcccaa tgctccggag actttctcca gatggacaat     1920
ttaatgccag agtaggtgta agatatttaa attaattatt taaatgtgta tatatcgcca     1980
ccaaattatt tatggttctg t                                              2001
```

<210> SEQ ID NO 2
<211> LENGTH: 2000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
agatggaaga ggcagggtcg gtgatgttta aaaaaagtcc tgaggtgatg gcaaacattt       60
aattttaatg aatgactttt tagagtttat acaaaatgac cttagctcgc taccagaaat      120
gctccgaatg ttttgtcaag actttaatgc tctcctagga tgtttctgaa ccacctccca      180
aattaacttt atgggagtct acagacagca agactggaaa aggctgattg gagtttgtgt      240
```

```
ctttcgcatt ccttttaaa actctttgtt cgaatgcaaa tcatctactt aaaatactgt    300
ccttaaacca aggccttgga ggaggaagga agccgctcgt gaagcctgat ggctggactg    360
tacatctcaa ccggccgtcc ccgtccgtgc ggtgaaataa aaaatgtttt caattttaaa    420
ttgcgtccta ggctccagga gtcttgagca gaggggatgc tcccaggtct cggtgctgat    480 ggggggggagg gggcggggct ggaatgtgtg acattcggt atttcaaata ctcgcctcct    540
aagtcttagc tgccttggga tgatggcacg atgtctcatc tcagagccca atccgattgt    600
caggaacgaa gatgtcttaa gtgcagaatg tggtgatcct tggccacttg ctagtcagcg    660
agccttgtgg gaagcgtata gagatgtcat tggacctctg caatatcgct aagtgttttc    720
tactgtcgtg atgggatcta aggtttctgt actttccgcg gtttgcagga tctgtctgta    780
gttttataca ggtgctgagc cctattgtga tgtatgtgct gtgcacattg acatatgccg    840
aataaatgga aacatttgtc atgtatgaaa agaaccccat tggacttgat gtaaagaacc    900
ggggaaggta ttgaaaacga ttaaaacctg cctggaaatg ccatgctaaa aaaaaaaaaa    960
aaaaaaaaaa aaaaaaaaaa aaaaaaaaaa agtgctttga actcttcaaa gaaaagacac   1020
ctcaaaatct acagcataat tgaggtatca gattttttgcc actttttact attatgattt   1080
tattcactag catttatttt gtcatctaga attttattca caagcaaaag cttttaggaa   1140
atcatactta ttttaggtta aatgagaaaa acattagct taatttttttc ttagttttttt   1200 taatgtttct gactatgata taatacctca caatagctta taaagtgaat tttcaatttc   1260
agtcattatt aatttggctg tctcaaaatc aggctatatg ttattcaagt accactcttt   1320
agtgtcgtga aaaaaatcag tacagtgggt tcaaaaacaa acatcttaat tgcagacact   1380
tgcaaatagt tcagagtatg tgttaatatg acatctgtaa catttcagat atttcttgtt   1440
ctcagttttt aaaaaagcaa tctaaaaagc aacggaacaa agggaaaata ttgacaagta   1500
atctgcttaa aaacccatgt gaatacgtgg aaatgtcaga tctttacaca ctgtaatctt   1560
gaacttccca tgttttatat gctaaacatt ctagcctctt gttagttacc aggtctttta   1620
aaattgtatg ggattacatt catatttaag attgtattct gattttgcat ggactaaata   1680
aaaatctact tatttagact gacagtaatt tcactgtcat tctgcaagtt gggttttgta   1740
gttttagtaa tcaaaagtag gtttactttt ttaaaaaact gtaattcagg tgtggtatag   1800
aaaataaact caagtgggta agaaacatct cagttcttat tgcctttaaa tgaaaattaa   1860
actaactgat ttcaacctca tcagacttcc aggaaaccca atctcaatca gtgatggagt   1920
ccctgattct cttaggatca tagcatctgg gaagttcaca tggtattgga taaggaaaag   1980
ggcctctgct ggctaggcca                                                2000
```

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtgtttgcat ggaggaaggt                                                  20

<210> SEQ ID NO 4
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 4
ctgagcaaga acgggaagac                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agcctgatgg ctggactgta                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtccgtgcgg tgaaataaaa                                                  20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgctgtagat tttgaggtgt ctt                                              23

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctgattttg agacagccaa a                                                21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttgatgccca ggaggtagtc                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tgagtgggtt aagggtttcg                                        20

<210> SEQ ID NO 11
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
tctttctaga aaatggaata tgttaagata attcctattc aagtgctttg aggcgcaggg   60
aggcgcgcac cgctccgcag ggtcccagcc cggccgcgcg                        100

<210> SEQ ID NO 12
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaaaagtgc tttgaactct tcaaagaaaa gacacctcaa aatctacagc ataattgagg   60
tatca                                                              65

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acagctggca tggtcagtta                                        20

<210> SEQ ID NO 14
<211> LENGTH: 11
<212> TYPE: DNA
<213> ORGANISM: Unknown
<220> FEATURE:
<223> OTHER INFORMATION: Description of Unknown:
      TSD sequence

<400> SEQUENCE: 14
aagtgctttg a                                                 11

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctctgtggac ctctttcaac g                                      21

<210> SEQ ID NO 16
<211> LENGTH: 20
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 16
tgcttgctcc agctctgtta                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaatggcata tgggctgagt                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cactgttggc agtcctcaaa                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atgctacacc actccctgct                                              20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgacaccagt gagaattgca t                                            21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttggccataa ttttccttgg                                              20

<210> SEQ ID NO 22
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 22
tctgcaaaac agcttgcatt                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaagccggtt gttgatgaag                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atccttgcca aaactgatgg                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttgggaatgt caaaccactg                                              20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcgctccgca ccgagtcc                                                18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctccatgcag cccgggta                                                18

<210> SEQ ID NO 28
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 28
agggccaagt gtccaataca                                              20

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gttccctcca tttcggttt                                               19

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ttctgtcgga ccaagaggac                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aggctcagaa gctgaacgag                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cctacagcct ggagctgttc                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aagcaactgc caaaccaaag                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
gggctgtact ggctcattgt                                         20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tggccatctc tgctcctact                                         20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttgtggaaaa ggatgccaat                                         20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ctacagggga cgacagaagg                                         20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gactacctcc tgggcatcaa                                         20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tcactggtga gaaccccct                                          19

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 40
ccatcatgaa agccaatggt                                                    20

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tctggtgtcc attggtctag g                                                  21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggcttttgga ttggacaaga                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gttctctcag ggggaaaagc                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agagcagcac acccaagtct                                                    20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
acctcagaac cagcacctgt                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 46
ggcggtgctg ttcttgtact                                                20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ctgcttctgc tctggtgaga                                                20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gtcttcccgt tcttgctcag                                                20

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cctgattcac acggcgtag                                                 19

<210> SEQ ID NO 50
<211> LENGTH: 13
<212> TYPE: DNA
<213> ORGANISM: Unknown
<220> FEATURE:
<223> OTHER INFORMATION: Description of Unknown:
      TSD sequence

<400> SEQUENCE: 50
aagtcagaca gag                                                       13
```